(12) United States Patent
Allen et al.

(10) Patent No.: US 7,250,054 B2
(45) Date of Patent: Jul. 31, 2007

(54) SYSTEMS, METHODS, AND APPARATUSES FOR CLAMPING AND RECLAMPING AN ORTHOPEDIC SURGICAL CABLE

(75) Inventors: C. Wayne Allen, Southaven, MS (US); Kevin Belew, Hernando, MS (US); Alisha Bergin, Southaven, MS (US); Phil Frederick, Memphis, TN (US); Jerry L. Jones, Memphis, TN (US); David C. Kelman, Collierville, TN (US); Richard D. Lambert, Germantown, TN (US); Terry McLean, Cordova, TN (US); Jeffrey J. Shea, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 321 days.

(21) Appl. No.: 10/230,040

(22) Filed: Aug. 28, 2002

(65) Prior Publication Data
US 2004/0087954 A1    May 6, 2004

(51) Int. Cl.
*A61B 17/56* (2006.01)
(52) U.S. Cl. .......................... 606/74; 606/103
(58) Field of Classification Search ............ 606/71–74, 606/86, 60, 103, 87, 151, 213
See application file for complete search history.

(56) References Cited

U.S. PATENT DOCUMENTS

| 575,631 A | 1/1897 | Brooke |
| 902,040 A | 10/1908 | Wyckoff |
| 2,501,978 A | 3/1950 | Wichman |
| 3,866,607 A | 2/1975 | Forsythe et al. |
| RE31,628 E | 7/1984 | Allgower et al. |
| 4,484,570 A | 11/1984 | Sutter et al. |
| 5,085,660 A | 2/1992 | Lin |
| 5,275,601 A | 1/1994 | Gogolewski et al. |
| 5,312,410 A | 5/1994 | Miller et al. |
| 5,324,291 A | 6/1994 | Ries et al. |
| 5,395,374 A | 3/1995 | Miller et al. |
| 5,415,658 A | 5/1995 | Kilpela et al. |
| 5,423,820 A | 6/1995 | Miller et al. |
| 5,431,659 A | 7/1995 | Ross, Jr. et al. |
| 5,470,333 A | 11/1995 | Ray |
| 5,527,310 A | 6/1996 | Cole et al. |

(Continued)

FOREIGN PATENT DOCUMENTS

DE    43 43 117 A1    6/1995

(Continued)

OTHER PUBLICATIONS

Brochure entitled Introducing Peak™ Polyaxial Anterior Cervical Plate, by Depuy Motech, one page, undated.

(Continued)

*Primary Examiner*—Eduardo C. Robert
*Assistant Examiner*—Annette Reimers
(74) *Attorney, Agent, or Firm*—Kilpatrick Stockton

(57) ABSTRACT

Systems, methods, and apparatuses for clamping and reclamping an orthopedic surgical cable used in conjunction with an orthopedic implant device, a bone, and/or bone implant or structure. Systems and methods provide a clamping body, a clamping mechanism, and a force application member that cooperate to allow tensioning and re-tensioning of a surgical cable.

26 Claims, 17 Drawing Sheets

U.S. PATENT DOCUMENTS

| | | |
|---|---|---|
| 5,536,127 A | 7/1996 | Pennig |
| 5,569,253 A | 10/1996 | Farris et al. |
| 5,601,553 A | 2/1997 | Trebing et al. |
| 5,665,088 A | 9/1997 | Gil et al. |
| 5,676,667 A | 10/1997 | Hausman |
| 5,702,399 A | 12/1997 | Kilpela et al. |
| 5,709,686 A | 1/1998 | Talos et al. |
| 5,788,697 A | 8/1998 | Kilpela et al. |
| 5,893,856 A | 4/1999 | Jacob et al. |
| 5,902,305 A | 5/1999 | Beger et al. |
| 5,935,130 A | 8/1999 | Kipela et al. |
| 5,935,133 A | 8/1999 | Wagner et al. |
| 5,954,722 A | 9/1999 | Bono |
| 5,964,769 A | 10/1999 | Wagner et al. |
| 5,968,046 A | 10/1999 | Castleman |
| 6,053,921 A * | 4/2000 | Wagner et al. ............... 606/74 |
| 6,129,730 A | 10/2000 | Bono et al. |
| 6,176,861 B1 | 1/2001 | Bernstein et al. |
| 6,193,721 B1 | 2/2001 | Michelson |
| 6,206,881 B1 | 3/2001 | Frigg et al. |
| 6,235,033 B1 | 5/2001 | Brace et al. |
| 6,306,136 B1 | 10/2001 | Baccelli |
| 6,306,140 B1 | 10/2001 | Siddiqui |
| 6,322,562 B1 | 11/2001 | Wolter |
| 6,355,043 B1 | 3/2002 | Adam |
| 6,358,250 B1 | 3/2002 | Orbay |
| 6,361,537 B1 | 3/2002 | Anderson |
| 6,364,885 B1 | 4/2002 | Kilpela et al. |
| 6,391,030 B1 | 5/2002 | Wagner et al. |
| 6,413,259 B1 | 7/2002 | Lyons et al. |
| 6,428,542 B1 | 8/2002 | Michelson |
| 6,440,135 B2 | 8/2002 | Orbay et al. |
| 6,454,769 B2 | 9/2002 | Wagner et al. |
| 6,475,218 B2 | 11/2002 | Gournay et al. |
| 6,506,191 B1 | 1/2003 | Joos |
| 6,520,965 B2 * | 2/2003 | Chervitz et al. ............... 606/74 |
| 6,595,994 B2 | 7/2003 | Kilpela et al. |
| 6,623,486 B1 | 9/2003 | Weaver et al. |
| 6,682,533 B1 | 1/2004 | Dinsdale et al. |
| 6,730,091 B1 | 5/2004 | Pfefferle et al. |
| 6,821,278 B2 | 11/2004 | Frigg et al. |
| 6,960,213 B2 * | 11/2005 | Chervitz et al. ............... 606/74 |
| 2001/0037112 A1 | 11/2001 | Brace et al. |
| 2001/0047174 A1 | 11/2001 | Donno et al. |
| 2002/0045901 A1 | 4/2002 | Wagner et al. |
| 2002/0058940 A1 | 5/2002 | Frigg et al. |
| 2002/0058943 A1 | 5/2002 | Kilpela et al. |
| 2002/0143338 A1 | 10/2002 | Orbay et al. |
| 2003/0016335 A1 | 1/2003 | Michelson |
| 2004/0044345 A1 | 3/2004 | DeMoss et al. |
| 2004/0073218 A1 | 4/2004 | Dehners |
| 2004/0097942 A1 | 5/2004 | Allen |
| 2004/0138666 A1 | 7/2004 | Molz, IV et al. |
| 2004/0199169 A1 | 10/2004 | Koons et al. |
| 2005/0070904 A1 | 3/2005 | Gerlach |
| 2005/0107796 A1 | 5/2005 | Gerlach et al. |
| 2006/0149265 A1 | 7/2006 | James |
| 2006/0167464 A1 | 7/2006 | Allen et al. |

FOREIGN PATENT DOCUMENTS

| | | |
|---|---|---|
| EP | 0 355 035 B1 | 2/1990 |
| EP | 0 486 762 B1 | 5/1995 |
| EP | 0 468 192 B1 | 9/1996 |
| EP | 0 760 632 B1 | 3/1997 |
| EP | 1169971 | 1/2002 |
| WO | WO 01/19267 A1 | 3/2001 |
| WO | WO 01/91660 | 12/2001 |
| WO | WO 02/058574 | 8/2002 |
| WO | WO 02/096309 A1 | 12/2002 |

OTHER PUBLICATIONS

Brochure entitled Introducing the Profile™ Anterior Thoracolumbar Compression Plate, by Dupuy Motech, one page, undated.

Baumgaertel, et al., "Fracture healing in biological plate osteosynthesis," *Injury*, 29(Supp. 3):S-C3-S-C6 (1998).

Bolhofner, et al., "The Results of Open Reduction and Internal Fixation of Distal Femur Fractures Using a Biologic (Indirect) Reduction Technique," *Journal of Orthopaedic Trauma*, 10(6):371-377 (1996).

Farouk, et al., "Minimally invasive plate osteosynthesis and vascularity: preliminary results of a cadaver injection study," *Injury*, 28(Supp. 1):S-A7-S-A12 (1997).

Farouk, et al., "Minimally Invasive Plate Osteosynthesis: Does Percutaneous Plating Disrupt Femoral Blood Supply Less Than the Traditional Technique?", *Journal of Orthopaedic Trauma*, 13(6):401-406 (1999).

Frigg, et al., "The development of the distal femur Less Invasive Stabilization System (LISS)," *Injury, Int. J. Care Injured*, 32(S-C24-31 (2001).

Frigg, et al., "LCP: The Locking Compression Plate System," *Bone Zone* (undated).

Gerber, et al., "Biological internal fixation of fractures," *Arch. Orthop. Trauma Surg.*, 109:295-303 (1990).

Karnezis, et al., "'Biological' internal fixation of long bone fractures: a biomechanical study of a 'noncontact' plate system," *Injury*, 29(9):689-695 (1998).

Koval, et al., "Distal Femoral Fixation : A Biomechanical Comparison of the Standard Condylar Buttress Plate, a Locked Buttress Plate, and the 95-Degree Blade Plate," Journal of Orthopaedic Trauma, 11(7):521-524 (1997).

Krettek, et al., "Minimally invasive percutaneous plate osteosynthesis (MIPPO) using the DCS in proximal and distal femoral fractures," *Injury*, 28(Supp. 1):S-A20-S-A30 (1997).

Krettek, et al., "Intraoperative control of axes, rotation and length in femoral and tibial fractures," *Injury*, 29(Supp. 3):S-C-29-S-C39 (1998).

Marti, et al., "Biomechanical Evaluation of the Less Invasive Stabilization System for the Internal Fixation of Distal Femur Fractures," *Journal of Orthopaedic Trauma*, 15(7):482-487, 2001.

Miclau, et al., "A Mechanical comparison of the Dynamic Compression Plate, Limited Contact-Dynamic Compression Plate, and Point Contact Fixator," *Journal of Orthopaedic Trauma*, 9(1):17-22 (1995).

Rüedi, et al., "New Techniques in Indirect Reduction of Long Bone Fractures," *Clinical Orthopaedics and Related Research*, No. 347:27-34 (1998).

Schavan, et al., "LISS—The Less Invasive Stabilization System for Metaphyseal Fractures of Femur and Tibia," *OTA 98 Posters* (1998).

Mudgal, et al., 'Plate and Screw Design in Fractures of the Hand and Wrist,' *Clinical Orthopaedics and Related Research*, 445:68-80 (2006).

* cited by examiner

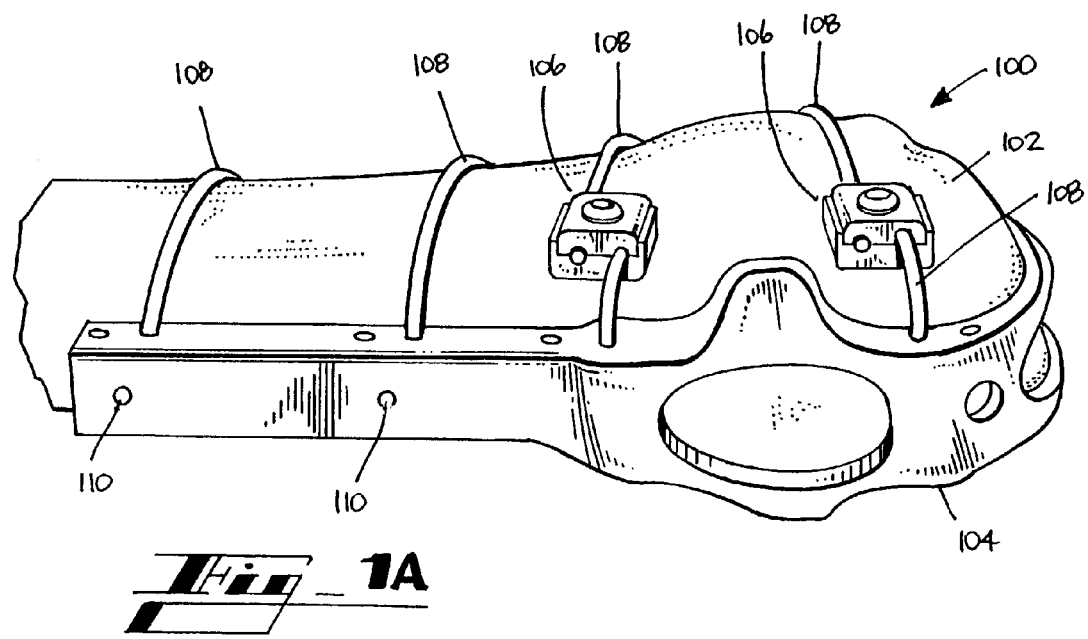
Fig_1A
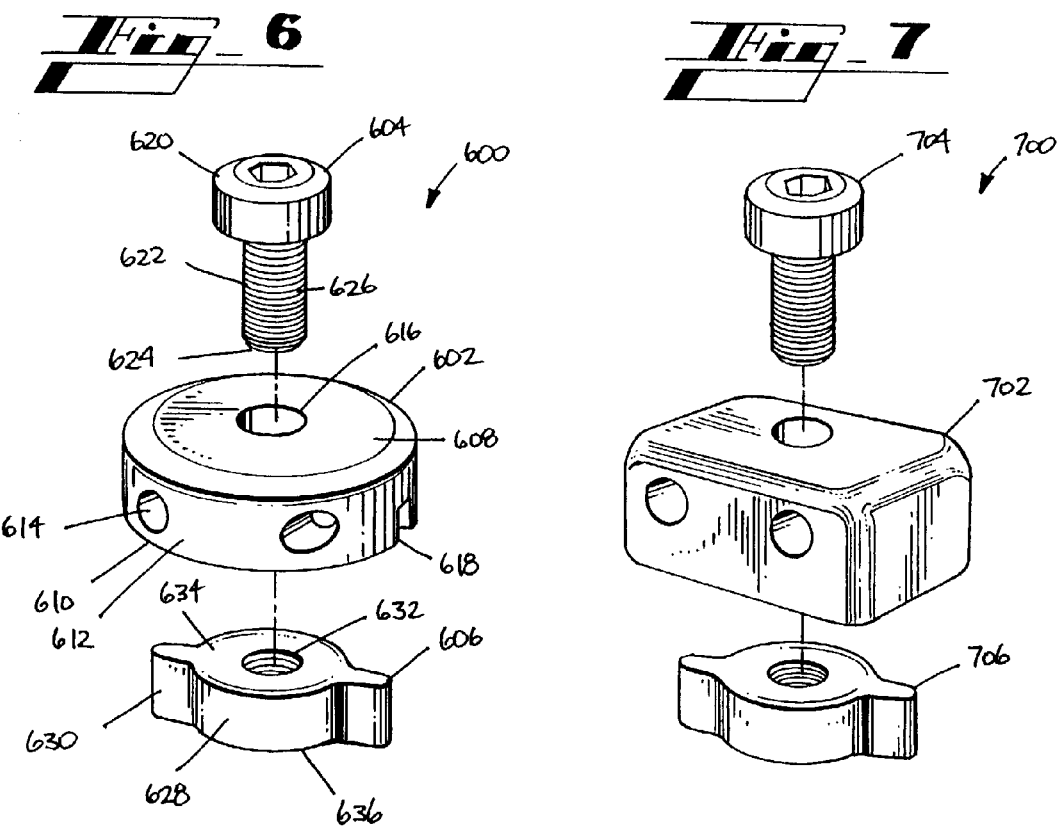
Fig_6
Fig_7

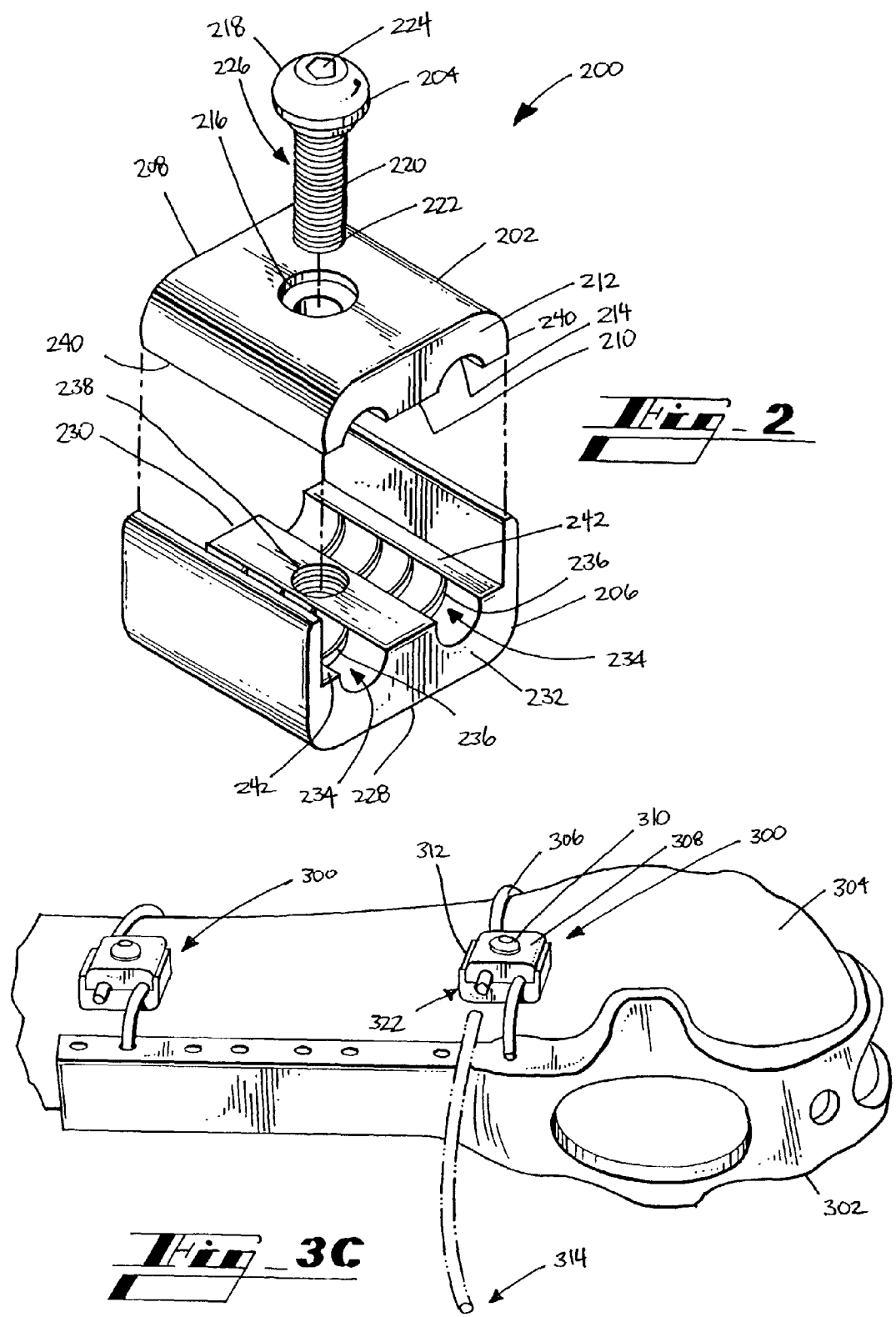

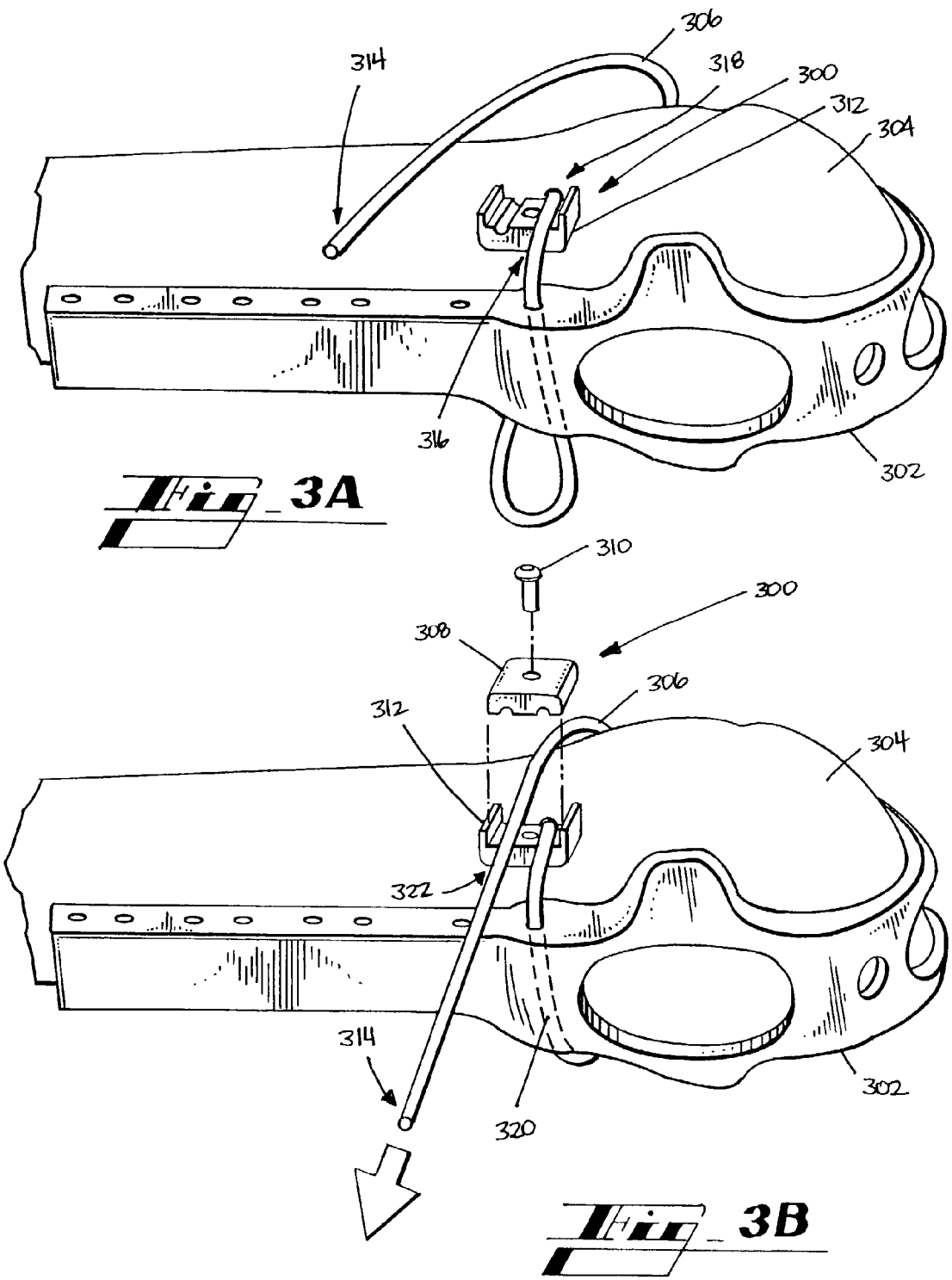

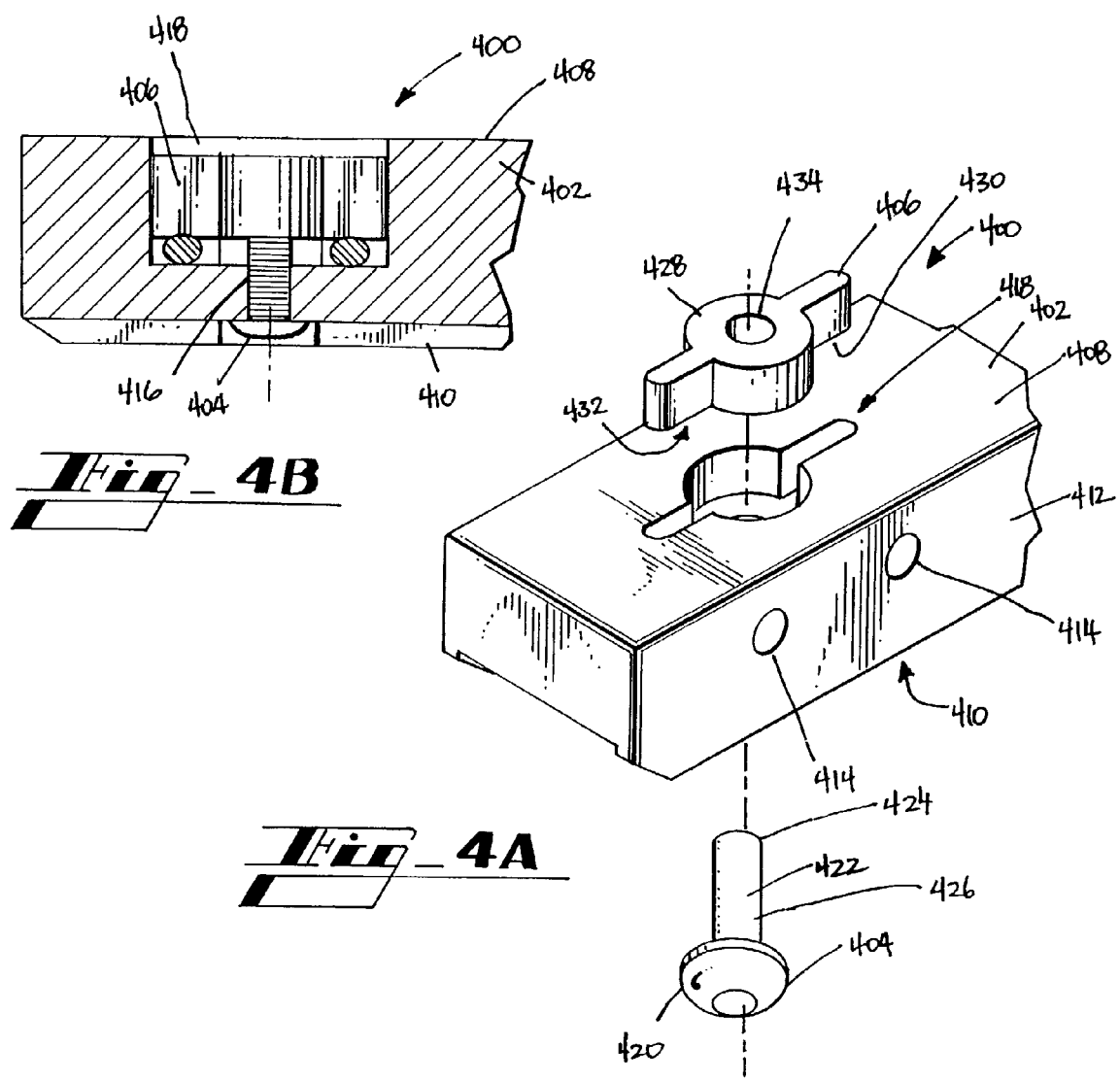
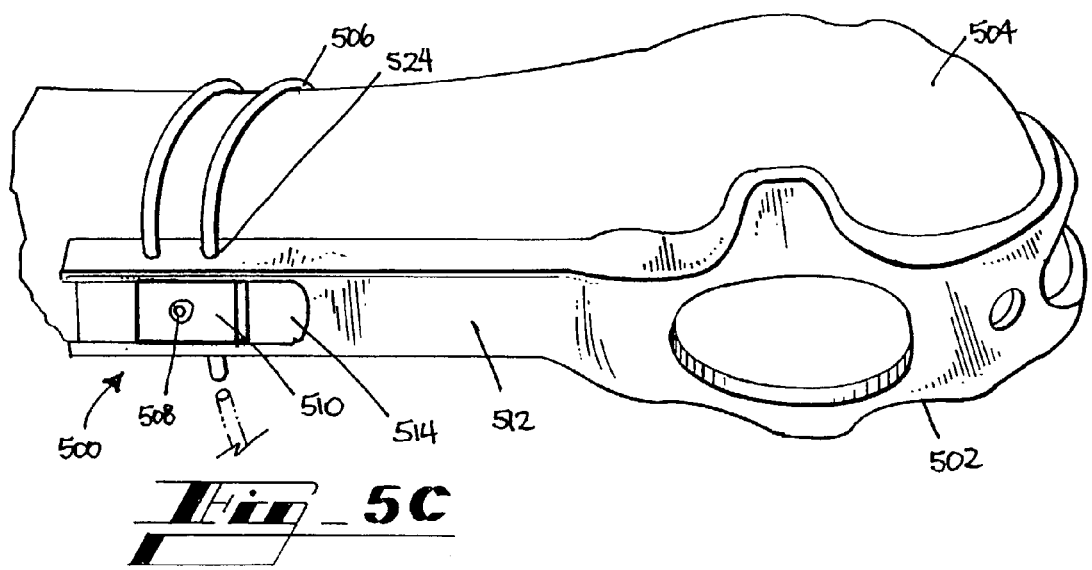

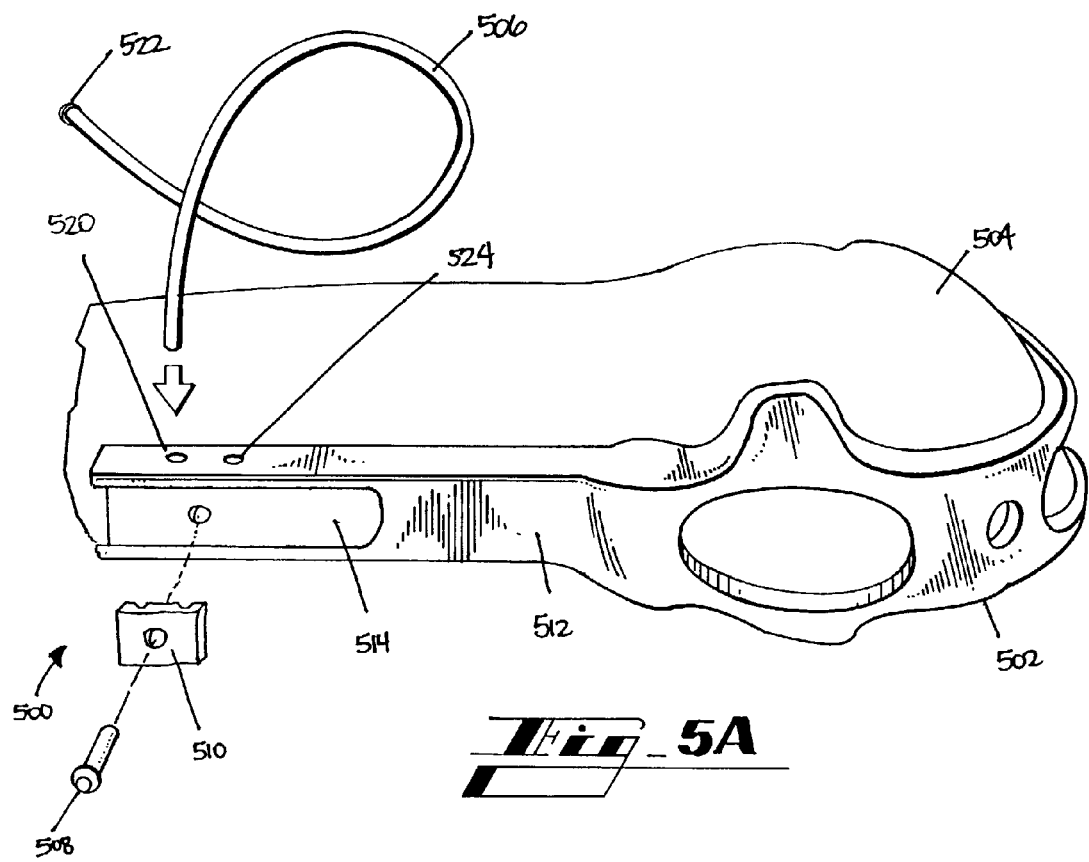
*Fig_5A*
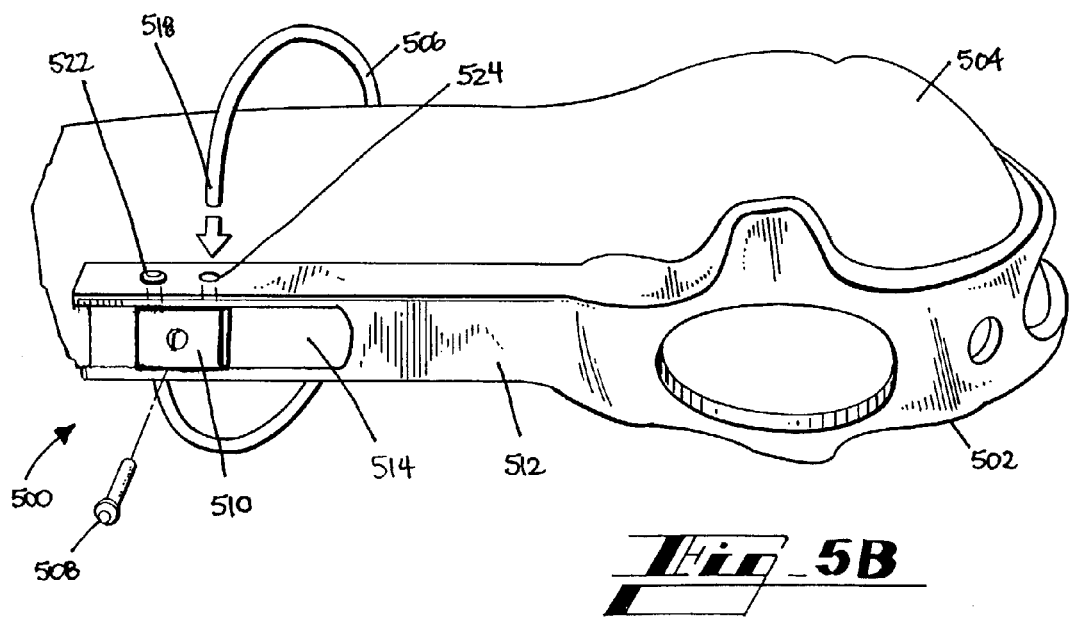
*Fig_5B*

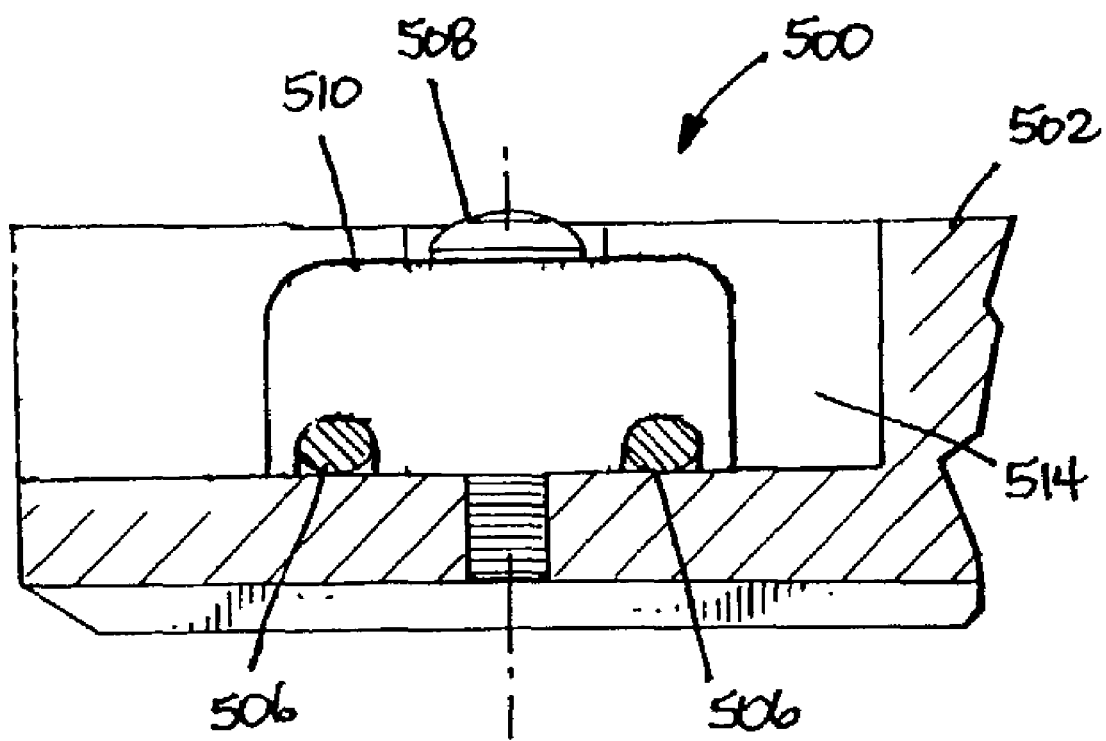
Fig_5D

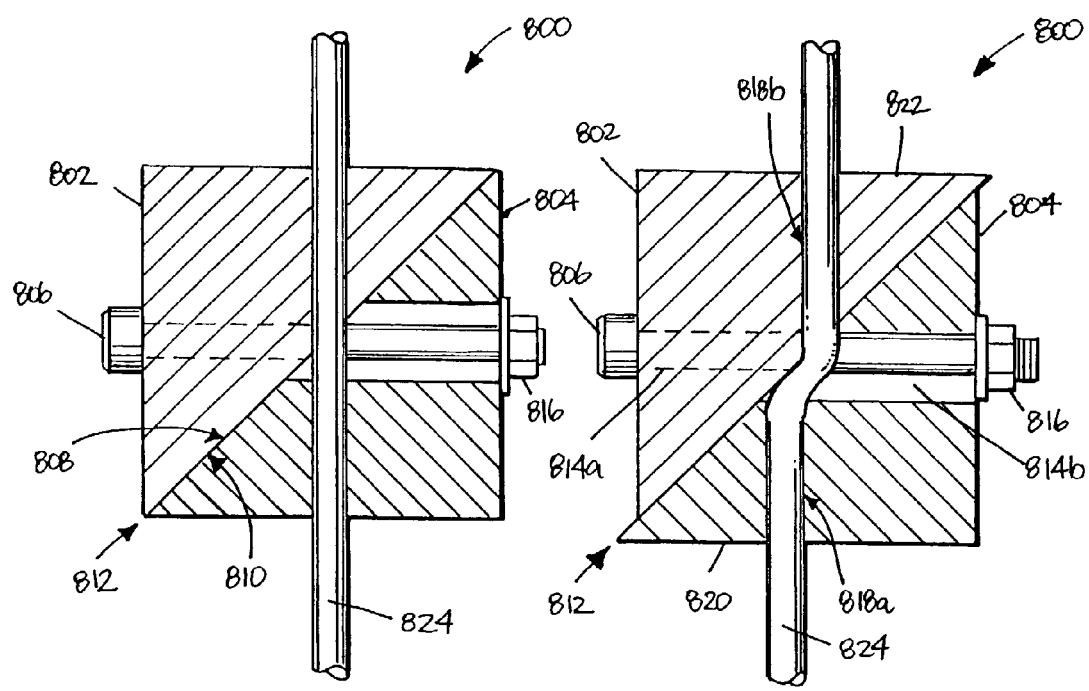
Fig_8A    Fig_8B
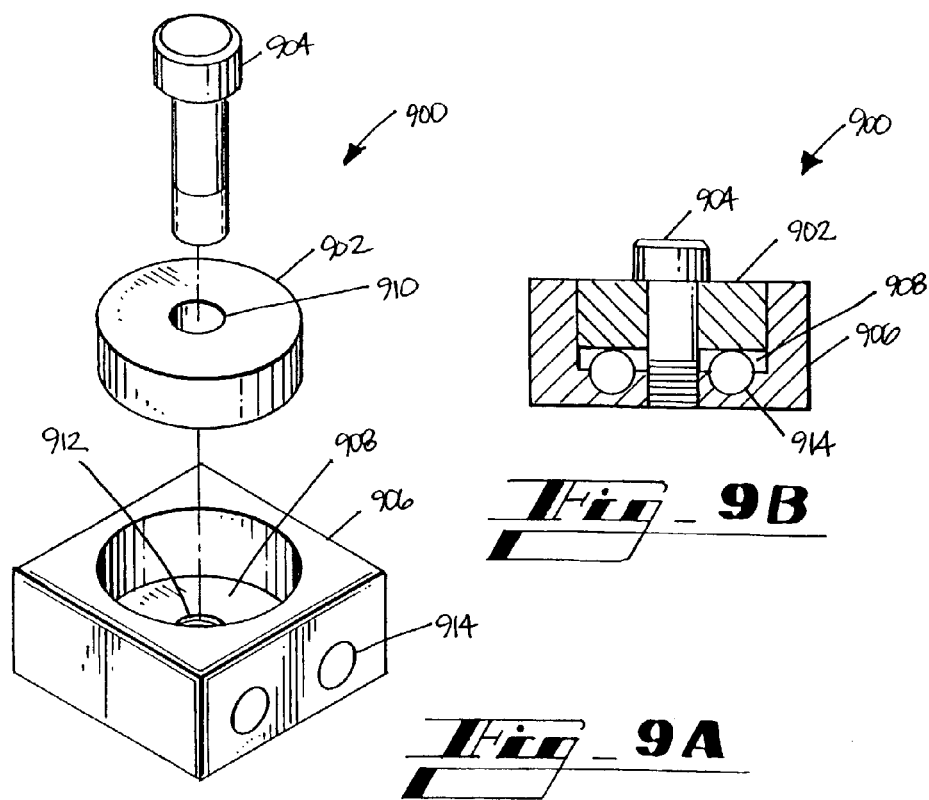
Fig_9A    Fig_9B

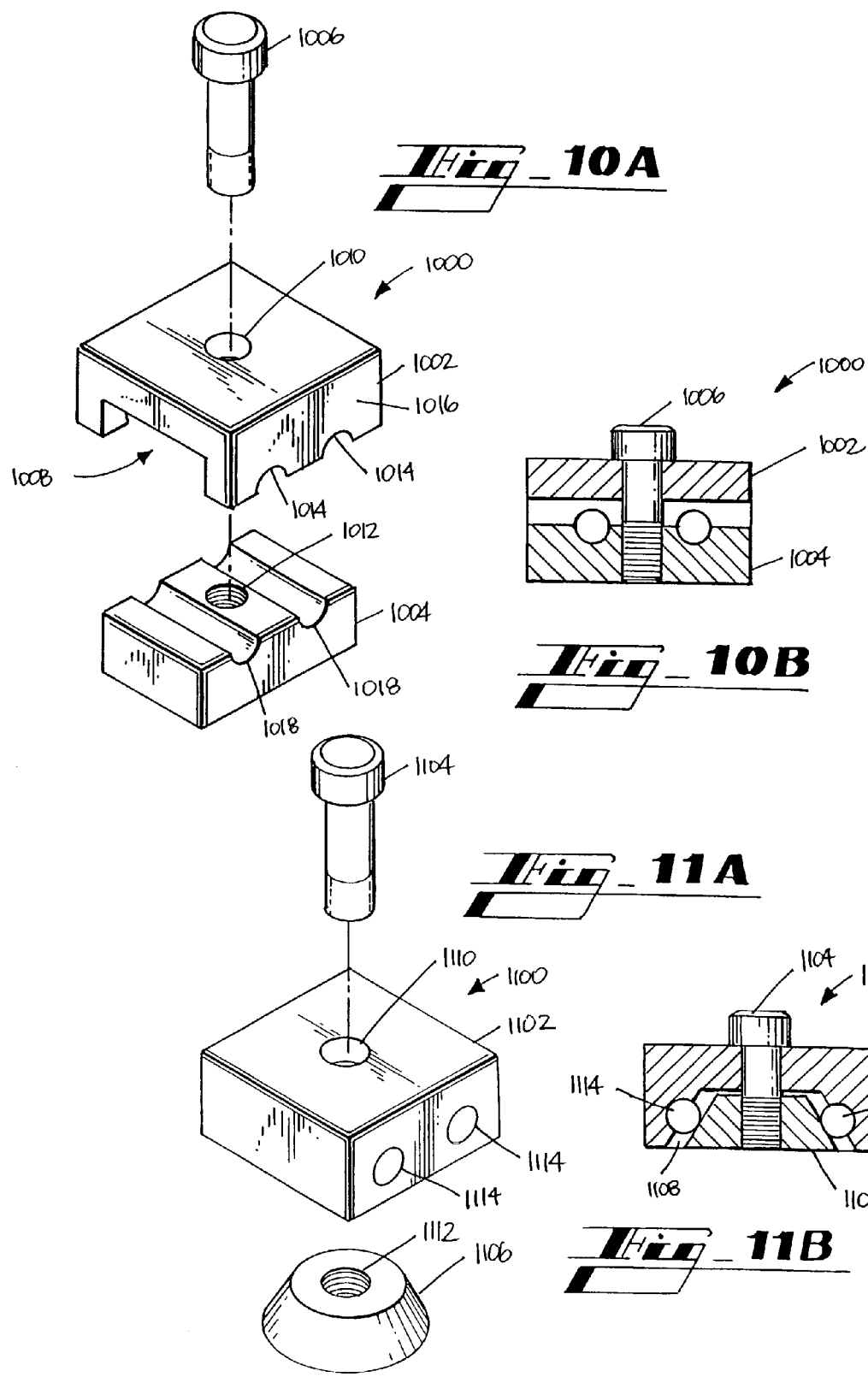

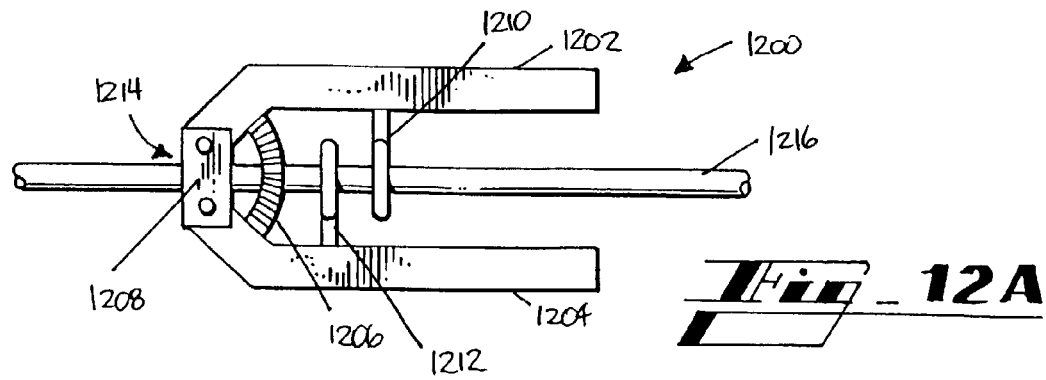
_Fig_12A
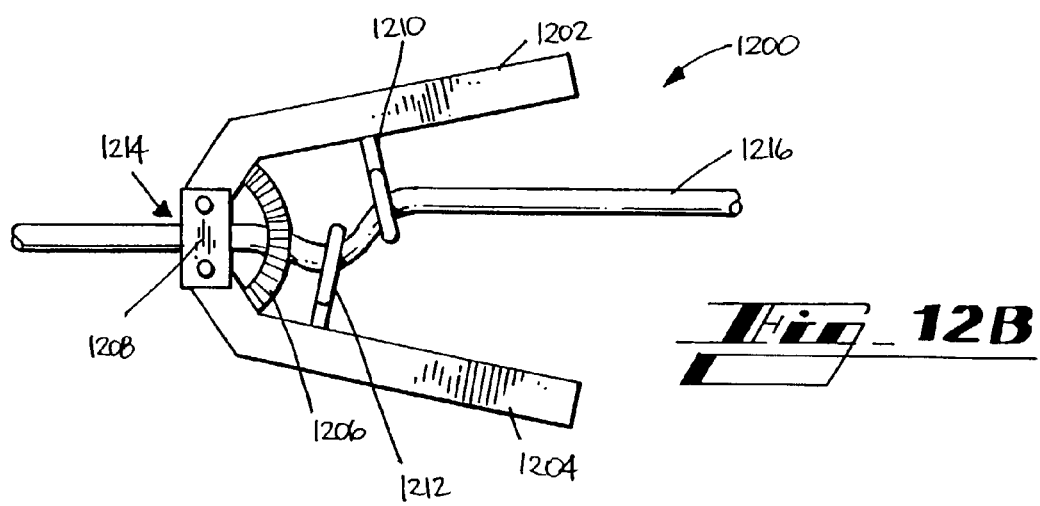
_Fig_12B
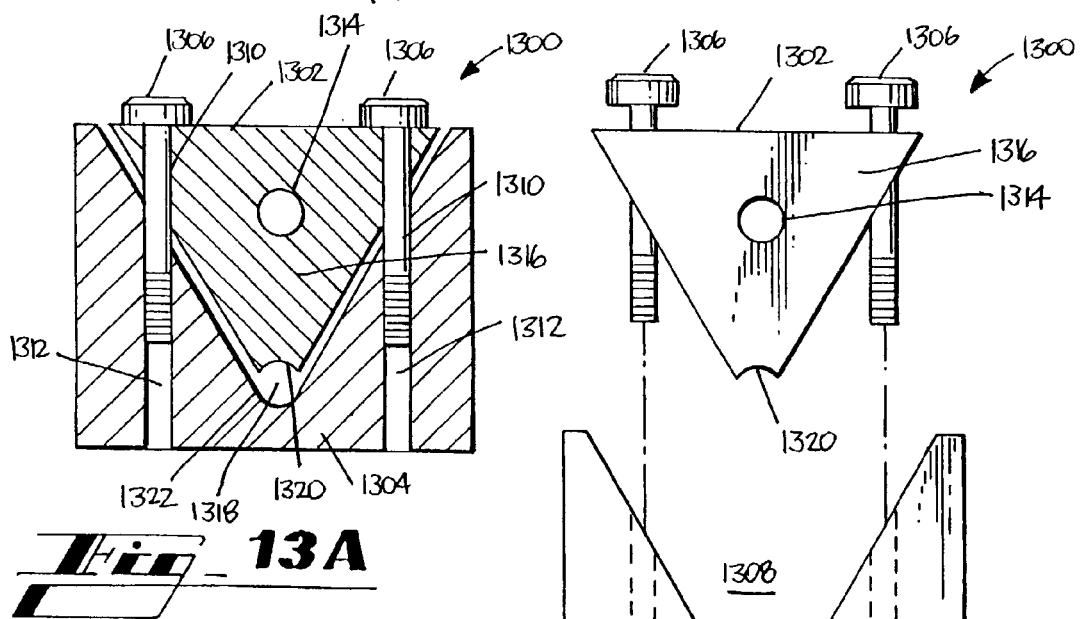
_Fig_13A
_Fig_13B

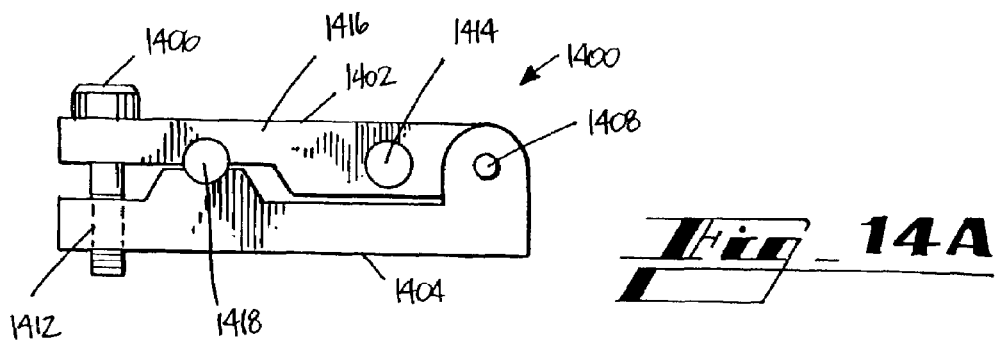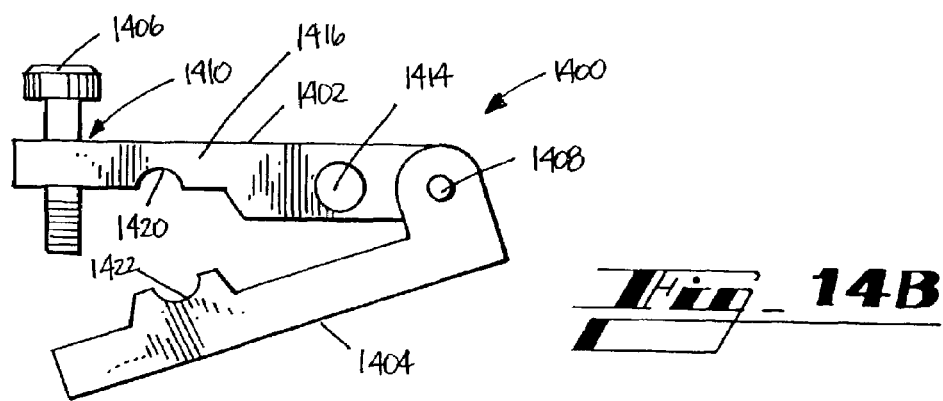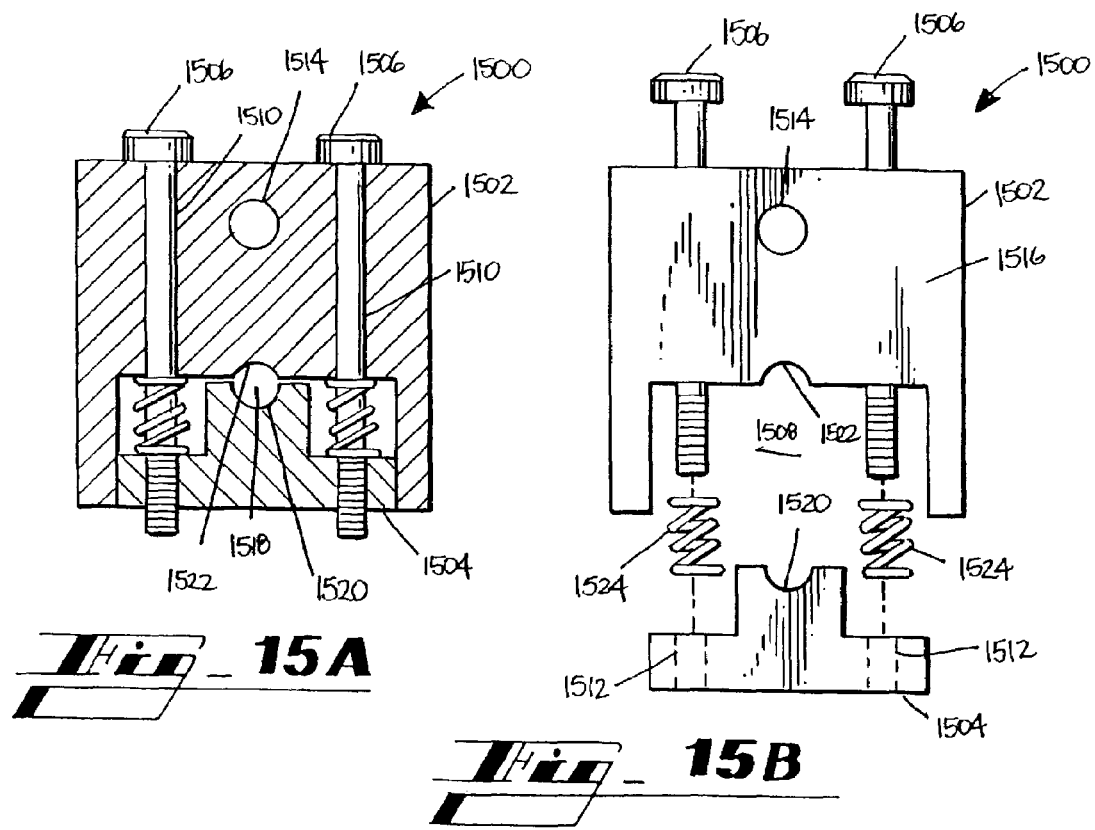

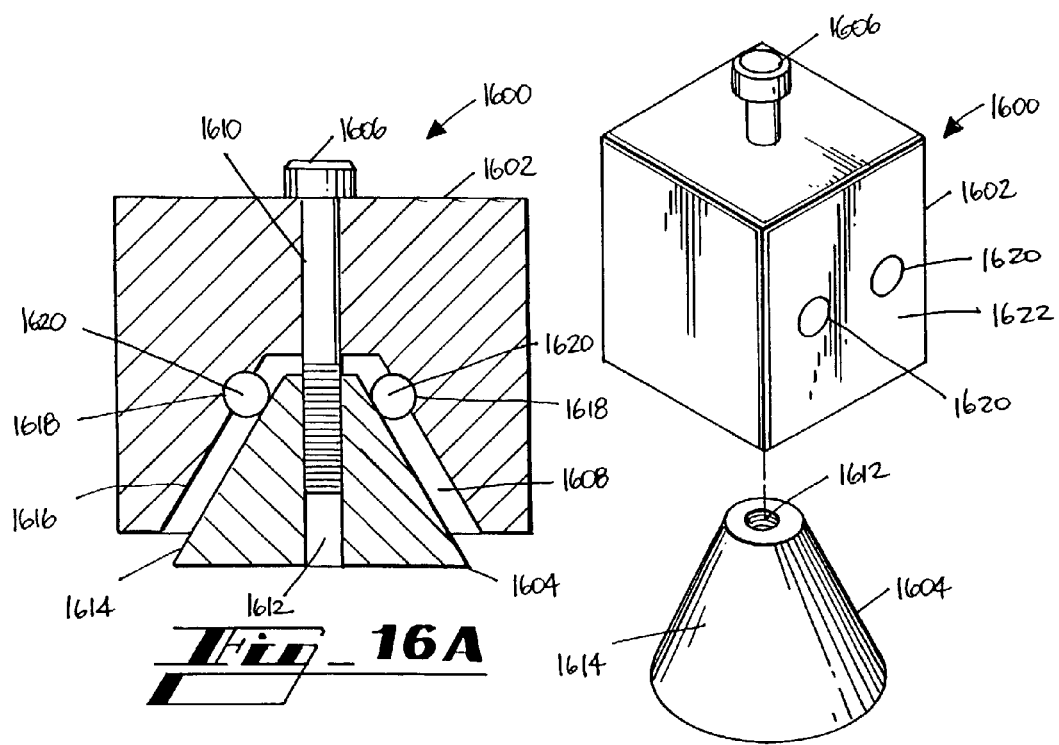
Fig. 16A
Fig. 16B
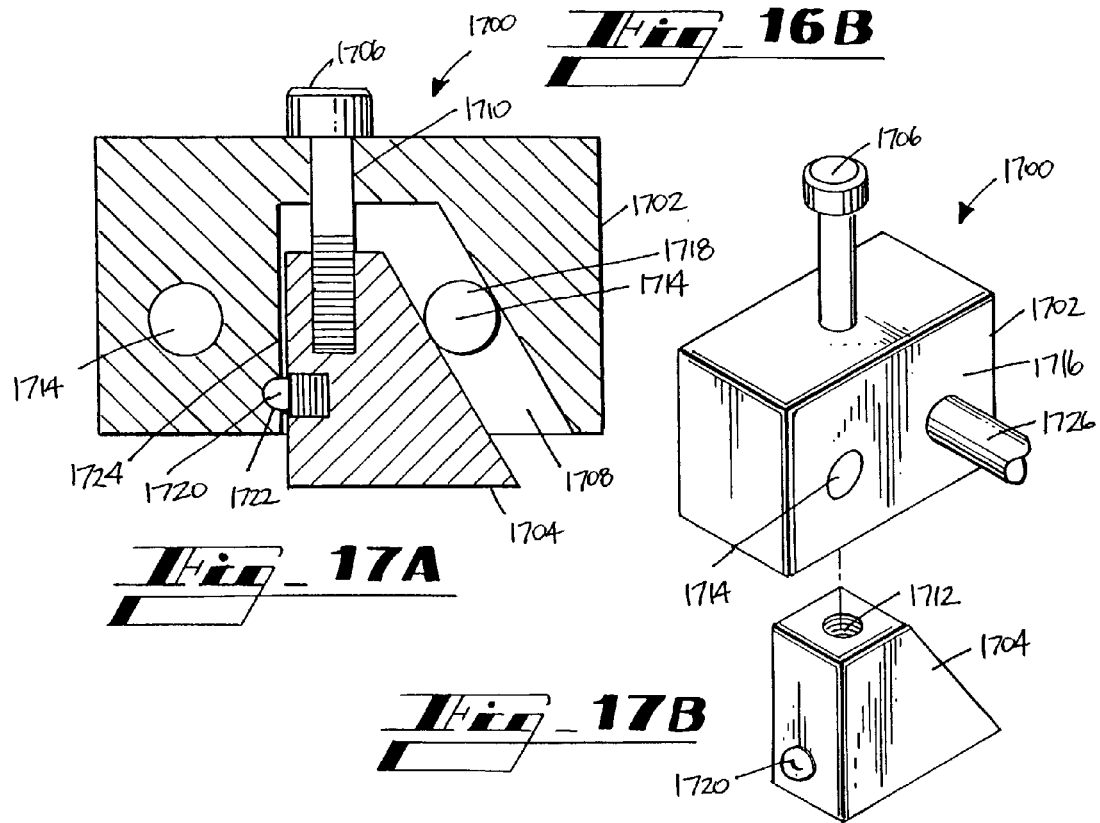
Fig. 17A
Fig. 17B

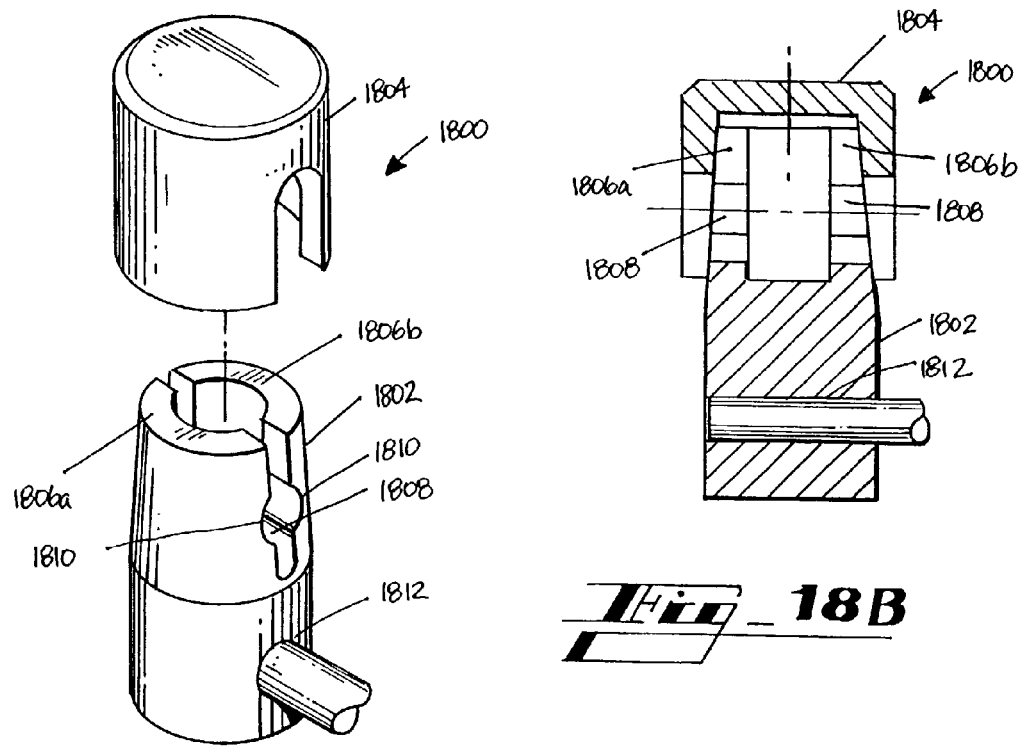
Fig_18A
Fig_18B
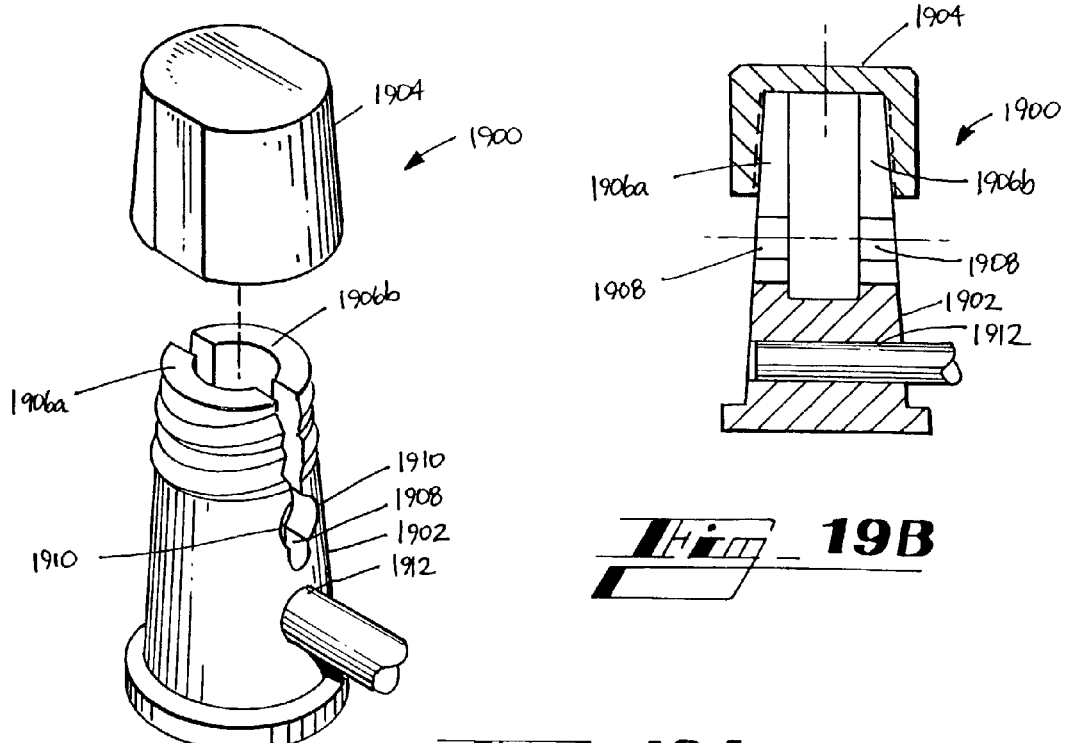
Fig_19A
Fig_19B

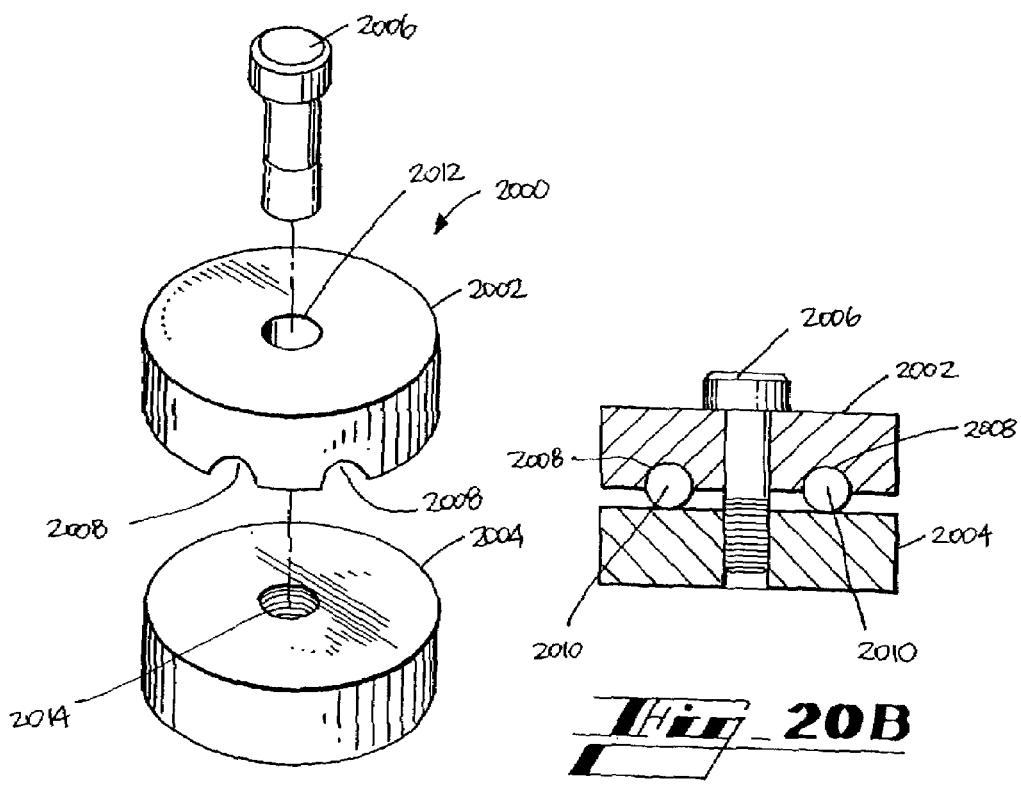
Fig_20A
Fig_20B
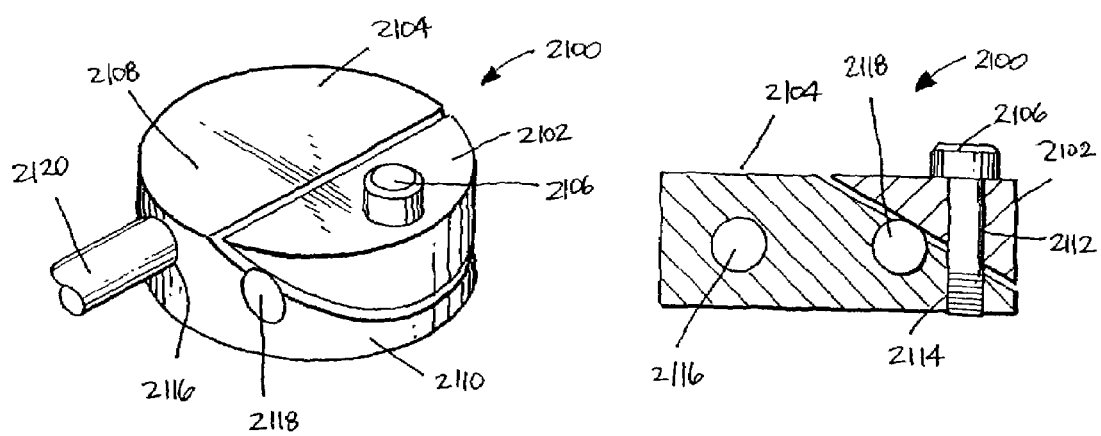
Fig_21A
Fig_21B

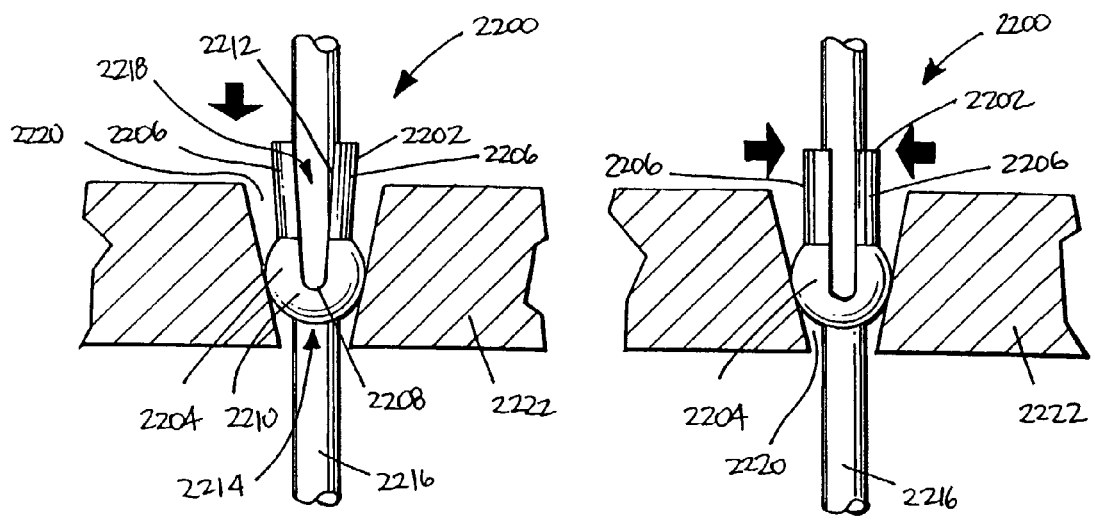
Fig_22A  Fig_22B
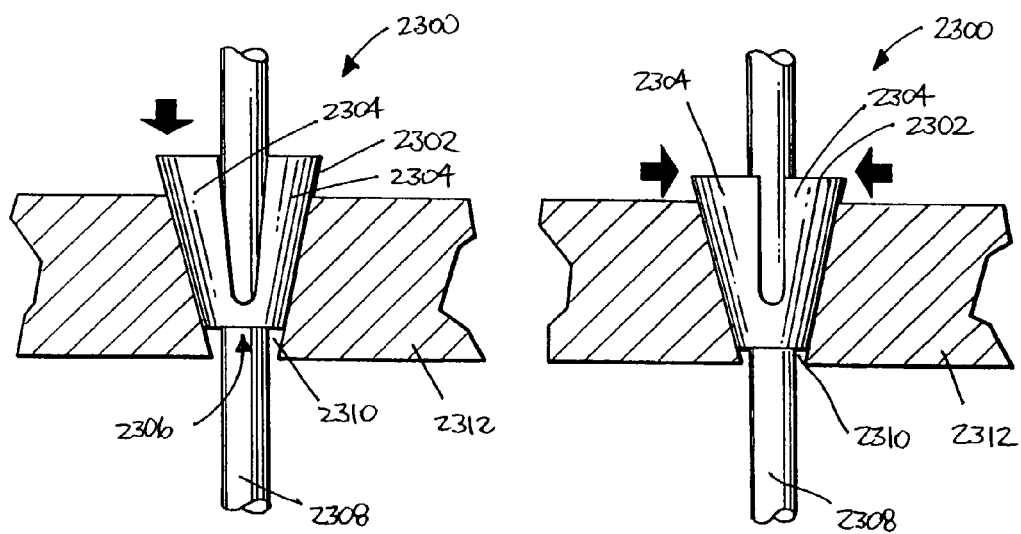
Fig_23A  Fig_23B

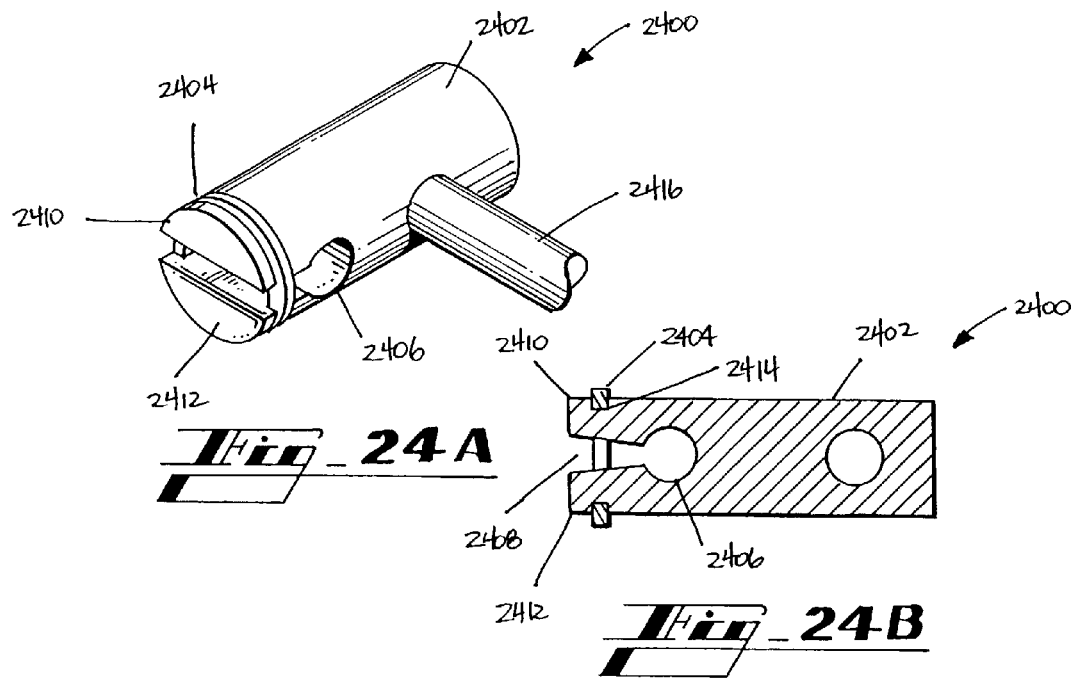
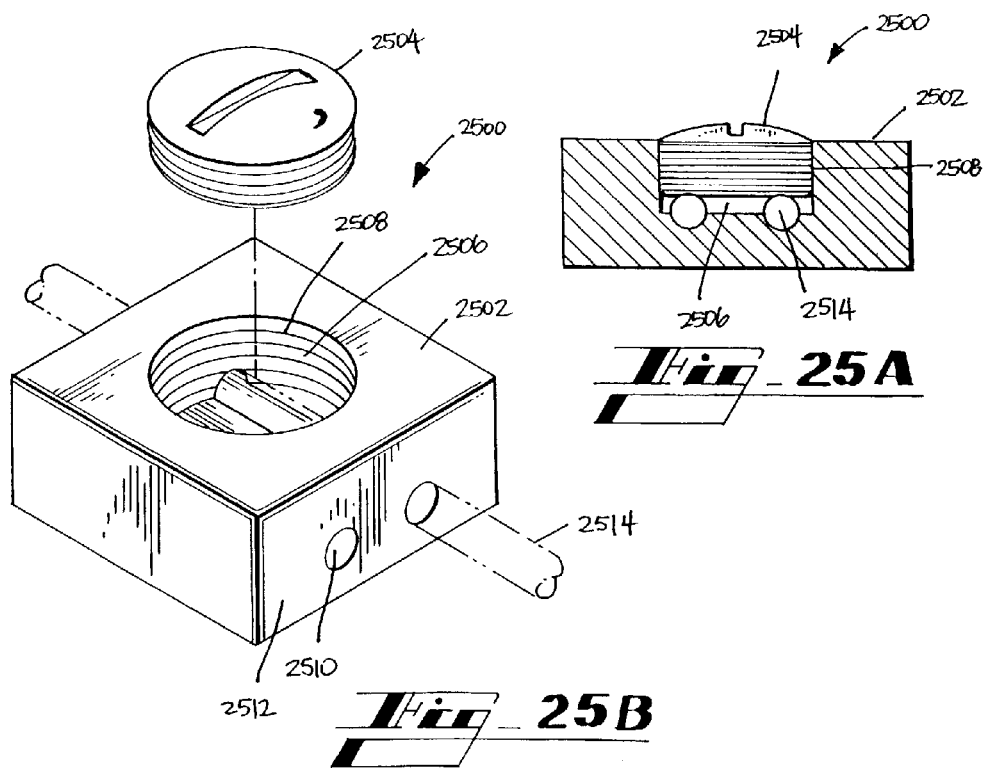

SYSTEMS, METHODS, AND APPARATUSES FOR CLAMPING AND RECLAMPING AN ORTHOPEDIC SURGICAL CABLE

FIELD OF THE INVENTION

The invention relates generally to systems, methods, and apparatuses related to orthopedic cable clamps, and more specifically to systems, methods, and apparatuses for clamping and reclamping an orthopedic surgical cable used in conjunction with an orthopedic implant device, a bone, and/or bone implant or structure.

BACKGROUND OF THE INVENTION

In an orthopedic surgical procedure, surgically implanted orthopedic cables are frequently used to secure bones together, or otherwise used to tie or fit other parts of the body together. An orthopedic cable is typically a thin length of cable that is manufactured from a biocompatible material such as cobalt chromium alloy, or stainless steel, or another similar type of material. Generally, an orthopedic cable is wrapped around an affected area of a patient's bone structure and then secured with a device such as a cable crimping device in order to stabilize the bone, secure fractures, stabilize trauma, install other devices to the bone, and for other purposes. Conventional orthopedic cable products utilize a device such as a cable crimping device to crimp the orthopedic cable in order to secure the cable with a specific tension around the affected area of a patient's body with a specific tension. However, crimping the cable typically causes damage to the cable and renders the cable unsuitable for re-use in an orthopedic procedure. It is not uncommon for an orthopedic cable to be replaced during the same surgical procedure when the tension on the orthopedic cable is insufficient and the cable must be retightened to obtain a sufficient tension. Since the orthopedic cable is damaged due to the crimping procedure, the orthopedic cable must be replaced. Replacing the orthopedic cable during a surgical procedure is time consuming for the surgeon and increases costs due to the wastage of the orthopedic cable.

In other instances, the conventional orthopedic cable product or portions of the product must also be replaced as well. In order to save time, manufacturers have designed single-use devices to secure the position of an orthopedic cable in a patient's body. These single-use devices cannot be reused and must be discarded if the orthopedic cable is initially tensioned and changes the tension or position of the surgical cable must be made later. Replacing the conventional orthopedic cable product or portions of the product during a surgical procedure is time consuming for the surgeon and increases costs due to the wastage of materials.

For example, one conventional orthopedic cable product utilizes a deformable sleeve or tube around the orthopedic cable. The metal sleeve or tube is then deformed by a screw that compresses the parts of the sleeve or tube around the cable. The metal sleeve or tube is deformed or crushed, and thus cannot be reused. Furthermore, the orthopedic cable may become deformed or crushed, and may not be suitable for re-use. In either event, once the surgical cable has been set to a desired position or tension, and for any reason becomes necessary to re-position or re-tension the surgical cable, then the metal sleeve or tube of the conventional orthopedic cable product must be replaced as well as the surgical cable.

In some instances, a conventional orthopedic cable product and an orthopedic cable are used in conjunction with an orthopedic device, a patient's bone, bone implant, or other structure. For example, an orthopedic device such as a trochanteric grip, can be secured to the exterior surface of a patient's femur using one or more orthopedic cables and corresponding conventional orthopedic cable products or devices. Each time an orthopedic cable is tensioned with respect to the patient's femur, the trochanteric grip becomes further secured to the exterior of the patient's femur. However, as each orthopedic cable is tensioned, other previously tensioned orthopedic cables may loosen, or the position of the orthopedic device may shift. In either instance, previously tensioned orthopedic cables may have to be re-tensioned or re-positioned with respect to the trochanteric grip and the patient's femur. Conventional orthopedic cable products or devices used to secure the position of the orthopedic cables may have to be replaced along with the orthopedic cables that have become damaged or crushed due to the installation of the orthopedic cable products or devices.

At least one conventional orthopedic cable product utilizes a releasable lever operated cable clamp to apply a clamping force to an orthopedic cable. The conventional orthopedic cable product tensions the cable to a desired tension, and a crimp is swaged onto the cable to hold the tension. Then the lever operated cable clamp releases the clamping force, and the cable clamp is removed from the cable. This type of conventional orthopedic cable product is not implantable within a patient's body. For example, the lever operated cable clamp is a separate component from the crimp, and is too large for implanting in a body. Such products utilizing a non-implantable clamp add to the complexity and time for performing relatively delicate surgical procedures.

SUMMARY OF THE INVENTION

Systems, methods, and apparatuses according to various embodiments of the invention address some or all of the above issues and combinations thereof. They do so by providing a surgical cable clamp for clamping and reclamping an orthopedic surgical cable used in conjunction with an orthopedic implant device, a bone, and/or bone implant or structure. The surgical cable clamp does not damage the orthopedic surgical cable when then the surgical cable clamp is operated or clamped with respect to the surgical cable. While the surgical cable is operated or in use, a tension can be maintained on the orthopedic surgical cable. Furthermore, the surgical cable clamp can be reused along with the same surgical cable when the surgical cable clamp is unclamped and reclamped with respect to the surgical cable, while retensioning the surgical cable with respect to the orthopedic implant device, a bone, and/or bone implant or structure. Such systems, methods, and apparatuses are particularly useful for surgeons installing an orthopedic surgical cable within a patient's body, and attempting to tension and retension the orthopedic cable with respect to the installation of an orthopedic implant device, a bone, and/or bone implant or structure in the patient's body.

One aspect of systems, methods, and apparatuses according to various embodiments of the invention, focuses on apparatuses for clamping and reclamping an orthopedic cable for installation in a patient's body. For purposes of this document, such apparatuses are each known as a "surgical cable clamp." A surgical cable clamp permits a surgeon to save time and reduce wastage during a surgical procedure by providing the option to reuse both a surgical cable clamp and orthopedic surgical cable that have been initially installed and tensioned. The surgeon may find that later during the same surgical procedure, the surgical cable clamp and orthopedic surgical cable should be retensioned, and the surgical cable clamp permits the surgeon to reclamp the orthopedic cable with respect to the installation of an orthopedic implant device, a bone, and/or bone implant or structure in a patient's body.

Another aspect of systems, methods, and apparatuses according to various embodiments of the invention, focuses on systems for clamping and reclamping an orthopedic cable for installation of a device in a patient's body. A surgical cable clamp permits a surgeon to save time and reduce wastage during a surgical procedure by providing the option to reuse both a surgical cable clamp and orthopedic surgical cable that have been used to initially install a device within a patient's body. The surgeon may find that later during the same surgical procedure, the surgical cable clamp and orthopedic surgical cable should be retensioned, or the device must be repositioned with respect to the patient's body. The surgical cable clamp permits the surgeon to reclamp the orthopedic cable with respect to installation of the device in the patient's body.

According to another aspect of the invention, systems and apparatuses according to various embodiments of the invention include in a combination with an orthopedic cable, apparatus for clamping and reclamping an orthopedic cable for installation with respect to a patient's body. The apparatus includes a clamping body adapted to positioning with respect to a patient's body, and an orthopedic cable. The apparatus further includes a clamping mechanism adapted to secure the orthopedic cable to the clamping body, secure a first tension in the orthopedic cable, release the tension in the orthopedic cable; and re-secure the orthopedic cable relative to the clamping body to secure another tension in the orthopedic cable.

According to yet another aspect of the invention, systems and apparatuses according to various embodiments of the invention can include an orthopedic cable and a surgical cable clamp. The surgical cable clamp includes a clamping body and a clamping mechanism. The clamping body is adapted to receive a portion of the orthopedic cable. The clamping mechanism is adapted to contact a portion of the clamping body, create a compression force on the portion of the orthopedic cable to secure the orthopedic cable relative to the clamping body with a first tension, release the compression force on the portion of the orthopedic cable so that the orthopedic cable can be released relative to the clamping body, and create a second compression force on the portion of the orthopedic cable to re-secure the orthopedic cable relative to the clamping body with a second tension.

According to yet another aspect of the invention, systems and apparatuses according to various embodiments of the invention can include an orthopedic cable, a surgical cable clamp, and a device. The device includes a surgical cable clamp with a clamping body and clamping mechanism. The clamping body is adapted to receive a portion of the orthopedic cable. The clamping mechanism is adapted to contact a portion of the clamping body, create a compression force on the portion of the orthopedic cable to secure the orthopedic cable relative to the device with a first tension, release the compression force on the portion of the orthopedic cable so that the orthopedic cable can be released relative to the clamping body, and create a second compression force on the portion of the orthopedic cable to re-secure the orthopedic cable relative to the device with a second tension.

A particular method for clamping and reclamping a surgical cable according to one aspect of systems and apparatuses of various embodiments of the invention includes mounting a portion of a surgical cable to the surgical cable clamp; applying a force to the portion of the surgical cable so that the surgical cable is secured relative to the surgical cable clamp with a first tension in the surgical cable; releasing the force on the portion of the surgical cable so that the surgical cable can be repositioned relative to the surgical cable clamp; and applying a second force to the surgical cable so that the surgical cable is again secured relative to the surgical cable clamp.

Another particular method for clamping and reclamping a surgical cable according to one aspect of systems and apparatuses of various embodiments of the invention includes securing a first portion of a surgical cable with a surgical cable clamp so that the first portion of the surgical cable remains in a stationary position relative to the surgical cable clamp; wrapping a remaining portion of the surgical cable around a part of a patient's body; connecting an extended portion of the surgical cable to the surgical cable clamp; applying a force to the extended portion of the surgical cable so that the surgical cable is secured relative to the surgical cable clamp with a first tension in the surgical cable; releasing the force on the extended portion of the surgical cable so that the surgical cable can be repositioned relative to the surgical cable clamp; and applying another force to the surgical cable so that the surgical cable is again secured relative to the surgical cable clamp.

Another particular method for using a surgical cable clamp with an orthopedic surgical cable for installation of a device with respect to a patient's body according to one aspect of systems and apparatuses of various embodiments of the invention includes securing a first portion of a surgical cable with a surgical cable clamp so that the first portion of the surgical cable remains in a stationary position relative to the surgical cable clamp; connecting the surgical cable to a device; wrapping a remaining portion of the surgical cable around a part of a patient's body; connecting an extended portion of the surgical cable to the surgical cable clamp; applying a force to the extended portion of the surgical cable so that the surgical cable and the device are secured relative to the surgical cable clamp with a first tension in the surgical cable; releasing the force on the extended portion of the surgical cable so that the surgical cable or device can be repositioned relative to the surgical cable clamp; and applying another force to the surgical cable so that the surgical cable and device are again secured relative to the surgical cable clamp.

Another particular method for using a surgical cable clamp with an orthopedic surgical cable for installation with respect to a patient's body according to one aspect of systems and apparatuses of various embodiments of the invention includes using a surgical cable clamp in combination with an orthopedic surgical cable to mount a portion of the orthopedic surgical cable to the surgical cable clamp; and to apply a force to the portion of the orthopedic surgical cable so that the orthopedic surgical cable is secured relative to the surgical cable clamp with a first tension in the orthopedic surgical cable. The method includes reusing the surgical cable clamp in combination with the orthopedic surgical cable to release the force on the portion of the orthopedic surgical cable so that the surgical cable can be repositioned relative to the surgical cable clamp; and to apply a second force to the orthopedic surgical cable so that the orthopedic surgical cable is again secured relative to the surgical cable clamp.

Objects, features and advantages of various systems, methods, and apparatuses according to various embodiments of the invention include:

(1) providing the ability to clamp and reclamp an orthopedic surgical cable without damaging the cable and creating the need to replace the cable;

(2) providing the ability to reuse a surgical cable clamp during the same surgical procedure;

(3) providing the ability to reuse the orthopedic surgical cable when the surgical cable clamp initially clamps the cable, and the cable needs to be retensioned or repositioned;

(4) providing the ability to reposition a device in a patient's body by reusing a surgical cable clamp and orthopedic surgical cable that have been initially used and tensioned, by retensioning the surgical cable by reclamping the cable with the surgical cable clamp; and (5) providing the ability to implant a device in a patient's body for clamping and reclamping a surgical cable.

Other objects, features and advantages of various aspects and embodiments of systems, methods, and apparatuses according to the invention are apparent from the other parts of this document.

BRIEF DESCRIPTION OF THE DRAWINGS

FIG. 1a is a perspective view of a structure that includes a surgical cable clamp in accordance with various embodiments of the invention.

FIG. 2 is an exploded perspective view of another structure for a surgical cable clamp in accordance with various embodiments of the invention.

FIGS. 3a-c illustrate a sequence for a method for using the surgical cable clamp shown in FIG. 2.

FIG. 4a illustrates an exploded perspective view of another structure for a surgical cable clamp in accordance with various embodiments of the invention.

FIG. 4b illustrates a cross-sectional view of the surgical cable clamp shown in FIG. 4a.

FIGS. 5a-d illustrate a sequence of another method for using a surgical cable clamp in accordance with various embodiments of the invention.

FIG. 6 is an exploded perspective view of another structure for a surgical cable clamp in accordance with various embodiments of the invention.

FIG. 7 is an exploded perspective view of another structure for a surgical cable clamp in accordance with various embodiments of the invention.

FIG. 8a is another view of a structure for a surgical cable clamp in accordance with various embodiments of the invention.

FIG. 8b is a cross-sectional view of the surgical clamp shown in FIG. 8a in a clamped position.

FIG. 9a is another view of a structure for a surgical cable clamp in accordance with various embodiments of the invention.

FIG. 9b is a cross-sectional view of the surgical cable clamp shown in FIG. 9a.

FIG. 10a is another view of a structure for a surgical cable clamp in accordance with various embodiments of the invention.

FIG. 10b is a cross-sectional view of the surgical cable clamp shown in FIG. 10a.

FIG. 11a is another view of a structure for a surgical cable clamp in accordance with various embodiments of the invention.

FIG. 11b is a cross-sectional view of the surgical cable clamp shown in FIG. 11a.

FIG. 12a is another view of a structure for a surgical cable clamp in accordance with various embodiments of the invention.

FIG. 12b is the surgical cable clamp shown in FIG. 12a in a clamped position.

FIG. 13a is another view of a structure for a surgical cable clamp in accordance with various embodiments of the invention.

FIG. 13b is a side exploded view of the surgical cable clamp shown in FIG. 13a.

FIG. 14a is another view of a structure for a surgical cable clamp in accordance with various embodiments of the invention.

FIG. 14b is a side exploded view of the surgical cable clamp shown in FIG. 14a.

FIG. 15a is another view of a structure for a surgical cable clamp in accordance with various embodiments of the invention.

FIG. 15b is an isometric view of the surgical cable clamp shown in FIG. 15a in an unclamped position cross section view.

FIG. 16a is another view of a structure for a surgical cable clamp in accordance with various embodiments of the invention.

FIG. 16b is an exploded perspective view of the surgical cable clamp shown in FIG. 16a.

FIG. 17a is another view of a structure for a surgical cable clamp in accordance with various embodiments of the invention.

FIG. 17b is an exploded perspective view of the surgical cable clamp shown in FIG. 17a.

FIG. 18a is another view of a structure for a surgical cable clamp in accordance with various embodiments of the invention.

FIG. 18b is a cross-sectional view of the surgical cable clamp shown in FIG. 18a.

FIG. 19a is another view of a structure for a surgical cable clamp in accordance with various embodiments of the invention.

FIG. 19b is a cross-sectional view of the surgical cable clamp shown in FIG. 19a.

FIG. 20a is another view of a structure for a surgical cable clamp in accordance with various embodiments of the invention.

FIG. 20b is a cross-sectional view showing the clamp position of the surgical cable clamp shown in FIG. 20a.

FIG. 21a is another view of a structure for a surgical cable clamp in accordance with various embodiments of the invention.

FIG. 21b is a cross-sectional view showing the clamp position of the surgical cable clamp shown in FIG. 21a.

FIG. 22a is another view of a structure for a surgical cable clamp in accordance with various embodiments of the invention.

FIG. 22b is a cross-sectional view showing clamp position of the surgical cable clamp shown in FIG. 22a.

FIG. 23a is another view of a structure for a surgical cable clamp in accordance with various embodiments of the invention.

FIG. 23b is cross-sectional view of the surgical cable clamp shown in FIG. 23a.

FIG. 24a is another view of a structure for a surgical cable clamp in accordance with various embodiments of the invention.

FIG. 24b is a cross-sectional view showing clamp position of the surgical cable clamp shown in FIG. 24a.

FIG. 25a is another view of a structure for a surgical cable clamp in accordance with various embodiments of the invention.

FIG. 25b is an exploded perspective view of the surgical cable clamp shown in FIG. 25a.

DETAILED DESCRIPTION OF SPECIFIC EMBODIMENTS

Figure 1B:
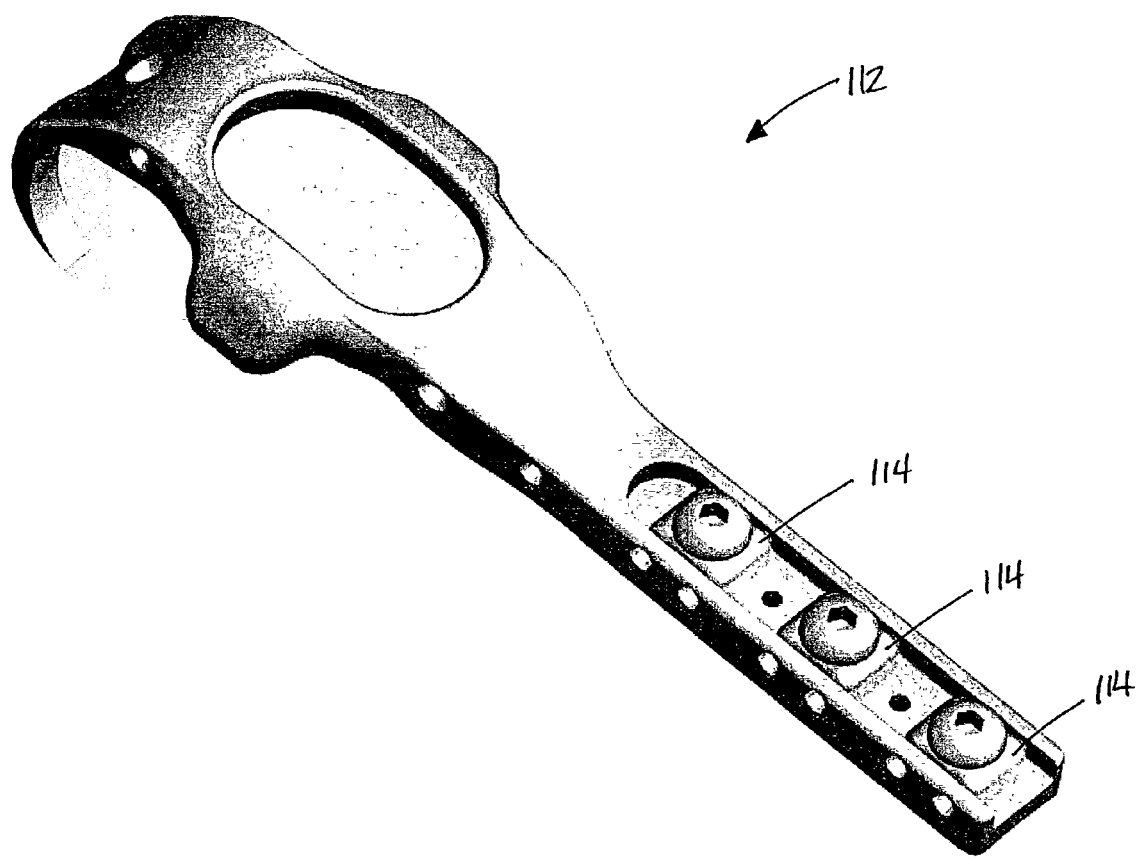
FIG. 1b is another perspective view of a structure that includes a surgical cable clamp in accordance with various embodiments of the invention.

Systems, methods, and apparatuses according to various embodiments of the invention address some or all of the above issues and combinations thereof. They do so by providing a surgical cable clamp for clamping and reclamping an orthopedic surgical cable used in conjunction with an orthopedic implant device, a bone, and/or bone implant or structure. The surgical cable clamp does not damage the orthopedic surgical cable when then the surgical cable clamp is operated or clamped with respect to the surgical cable. While the surgical cable is operated or in use, a tension can be maintained on the orthopedic surgical cable. Furthermore, the surgical cable clamp can be reused along with the same surgical cable when the surgical cable clamp is unclamped and reclamped with respect to the surgical cable, while retensioning the surgical cable with respect to the orthopedic implant device, a bone, and/or bone implant or structure. Such systems, methods, and apparatuses are particularly useful for surgeons installing an orthopedic surgical cable within a patient's body, and attempting to tension and retension the orthopedic cable with respect to the installation of an orthopedic implant device, a bone, and/or bone implant or structure in the patient's body.

FIG. 1a is a perspective view of a preferred environment for a surgical cable clamp in accordance with various embodiments of the invention. A preferred environment 100 shown in FIG. 1a is the proximal end of a human femur bone 102 in conjunction with a trochanteric grip 104 for use in a total hip replacement surgical procedure. In a first embodiment of the invention, a surgical cable clamp is a stand alone-type clamp 106 for securing the position of an orthopedic surgical cable 108 relative to a portion of the trochanteric grip 104 and a patient's femur bone 102. In a second embodiment of the invention, a surgical cable clamp is a device-incorporated clamp 110 for securing the position of an orthopedic surgical cable 108 relative to a portion of the trochanteric grip 104 and a patient's femur bone 102. The device-incorporated clamp 110 utilizes a portion of the trochanteric grip 104 or other prefabricated orthopedic device for clamping the orthopedic surgical cable 108.

Typically, a trochanteric grip 104 is secured at the proximal end of a patient's femur bone 102 during a total hip replacement procedure. One or more orthopedic surgical cables 108 can be utilized to secure the trochanteric grip 104 into a position relative to the proximal end of a patient's femur bone 102. When a force is applied to a surgical cable clamp 106, 110, the surgical cable clamp 106, 110 compresses the orthopedic surgical cable 108, thus securing the orthopedic surgical cable 108 into a position relative to the trochanteric grip 104 and patient's femur 102.

If necessary, the orthopedic surgical cable 108 can be loosened or otherwise retensioned by applying another force to the surgical cable clamp 106, 110 to relieve the compression force on the orthopedic surgical cable 108 applied by the surgical cable clamp 106, 110. The orthopedic surgical cable 108 can then be retensioned by hand or by way of a tensioning device (not shown) so that the orthopedic surgical cable 108 is at a desired tension or position. Yet another force can then be applied to the surgical cable clamp 106, 110 to create another compression force on the orthopedic surgical cable 108 which can then maintain the desired tension or position of the orthopedic surgical cable 108. Depending upon the location of the orthopedic surgical cable 108 relative to the trochanteric grip 104 and the patient's femur bone 102 or other bone, either and/or both the stand alone-type clamp 106 or the device-incorporated incorporated clamp 110 may be used to secure the position and tension of the orthopedic surgical cable 108 as shown.

A surgical cable clamp in accordance with the invention can have other configurations as shown and described in FIGS. 1b, 1c, 4, and 6-25. A surgical cable clamp can be either a stand alone-type clamp device or a device incorporated-type clamp device. Furthermore, as one skilled in the art will recognize, a surgical cable clamp can be fashioned as a single or multiple component-type clamp. In any configuration, a surgical cable clamp is used to secure a tension and, if necessary, secure another tension in an orthopedic surgical cable without need for replacing the original surgical cable. A surgical cable clamp in accordance with the invention can be used with other prefabricated orthopedic devices, such as a bone plate, that utilize orthopedic surgical cables for securing the device to a bone or another part of a patient's body. Finally, even though a surgical cable clamp in accordance with the invention is shown in FIG. 1a used in conjunction with an orthopedic surgical cable and a trochanteric grip, a surgical cable clamp can be utilized with one or more surgical cables, or incorporated into another type of orthopedic device to be secured to a portion of a patient's body such as a bone or another body structure.

FIG. 1b is a perspective view of a structure including a surgical cable clamp in accordance with the invention. The structure shown in FIG. 1b is a trochanteric grip 112 that can be installed adjacent to the proximal end of a human femur bone (similar to that shown in FIG. 1a as 102) for use in a total hip replacement surgical procedure. In another embodiment of the invention, a surgical cable clamp is a device-incorporated clamp 114 for securing the position of an orthopedic surgical cable (not shown) relative to a portion of the trochanteric grip 112 and a patient's femur bone. The device-incorporated clamp 114 utilizes a portion of the trochanteric grip 112 or other prefabricated orthopedic device for clamping the orthopedic surgical cable.

Similar to 104 in FIG. 1a, the trochanteric grip 112 is secured at the proximal end of a patient's femur bone during a total hip replacement procedure. One or more orthopedic surgical cables can be utilized to secure the trochanteric grip 112 into a position relative to the proximal end of a patient's femur bone. When a force is applied to a device-incorporated clamp 114, the device-incorporated clamp 114 compresses the orthopedic surgical cable, thus securing the orthopedic surgical cable into a position relative to the trochanteric grip 112 and patient's femur.

If necessary, the orthopedic surgical cable can be loosened by applying another force to the device-incorporated clamp 114 to relieve the compression force on the orthopedic surgical cable applied by the device-incorporated clamp 114. The orthopedic surgical cable can then be retensioned by hand or by way of a tensioning device (not shown) so that the orthopedic surgical cable is at a desired tension or position. Yet another force can then be applied to the device-incorporated clamp 114 to create another compression force on the orthopedic surgical cable which can then maintain the desired tension or position of the orthopedic surgical cable. Depending upon the location of the orthopedic surgical cable relative to the trochanteric grip 112 and the patient's femur bone or other bone, the device-incorporated clamp 114 may be used to secure the position and secure the tension of the orthopedic surgical cable.

Figure 1C:
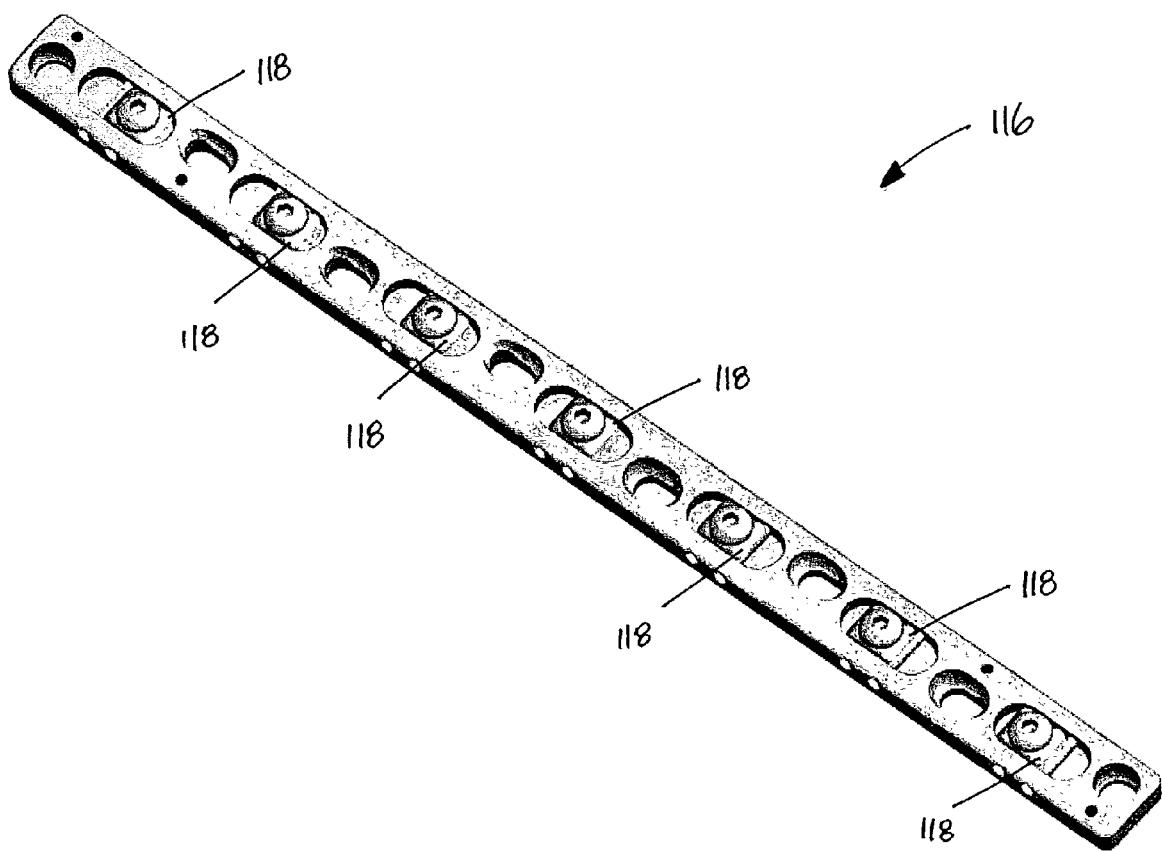
FIG. 1c is another perspective view of a structure that includes a surgical cable clamp in accordance with various embodiments of the invention.

FIG. 1c is a perspective view of another structure including a surgical cable clamp in accordance with the invention. The structure shown in FIG. 1c is a bone plate 116 that can be installed adjacent to a human bone for use in an orthopedic surgical procedure. In another embodiment of the invention, a surgical cable clamp is a device-incorporated clamp 118 for securing the position of an orthopedic surgical cable (not shown) relative to a portion of the bone plate 116 and a patient's bone. The device-incorporated clamp 118 utilizes a portion of the bone plate 116 or other prefabricated orthopedic device for clamping the orthopedic surgical cable.

The bone plate 116 is adjacent to a patient's bone during an orthopedic surgical procedure. One or more orthopedic surgical cables can be utilized to secure the bone plate 116 into a position relative to the patient's bone. When a force is applied to a device-incorporated clamp 118, the device-incorporated clamp 118 compresses the orthopedic surgical cable, thus securing the orthopedic surgical cable into a position relative to the bone plate 116 and patient's bone.

If necessary, the orthopedic surgical cable can be loosened by applying another force to the device-incorporated clamp 118 to relieve the compression force on the orthopedic surgical cable applied by the device-incorporated clamp 118. The orthopedic surgical cable can then be retensioned by hand or by way of a tensioning device (not shown) so that the orthopedic surgical cable is at a desired tension or position. Yet another force can then be applied to the device-incorporated clamp 118 to create another compression force on the orthopedic surgical cable which can then maintain the desired tension or position of the orthopedic surgical cable. Depending upon the location of the orthopedic surgical cable relative to the bone plate 116 and the patient's bone or other bone, the device-incorporated clamp 118 may be used to secure the position and secure the tension of the orthopedic surgical cable.

The device-incorporated clamps 114, 118 of FIGS. 1b and 1c are preferred embodiments of the invention. Other embodiments of the invention can also be used in the structure shown in FIGS. 1b and 1c to accomplish similar functions in accordance with the invention.

FIG. 2 is a perspective view of an embodiment of a stand alone-type clamp 200 similar to that shown as 106 in FIG. 1a. The embodiment of the stand alone-type clamp 200 shown here includes an upper clamping body 202, a clamping bolt 204, and a lower clamping body 206.

The upper clamping body 202 in this embodiment is rectangularly-shaped and has a relatively flat profile with a generally rounded upper surface 208 and a generally flat lower surface 210. On a lateral side 212 between the upper surface 208 and lower surface 210, a pair of semi-circular cable channels 214 are machined in the lower surface 210. The cable channels 214 are sized to receive the width of an orthopedic surgical cable (not shown) and are machined through the width of the upper clamping body 202 along the lower surface 210 to the opposing lateral side. Through the upper surface 208, a bolt hole 216 for receiving the clamping bolt 204 is machined through the thickness of the clamping body 202 to the lower surface 210. Note that the upper clamping body 202 can have numerous other shapes and configurations in accordance with the invention.

The clamping bolt 204 in this embodiment is shaped similar to a conventional machine screw with a socket head 218, a threaded body 220, and blunt point 222. The socket head 218 includes a recess 224 sized to receive a hexagonal-shaped tightening instrument (not shown) for tightening and untightening the clamping bolt 204 to a desired tension. Alternatively, the external shape of the socket head 218 can be shaped for tightening with a wrench-type instrument (not shown) for tightening and untightening a corresponding geometrically-shaped socket head. The threaded body 220 is sized to diametrically fit within the bolt hole 216 of the upper clamping body, and includes one or more threads 226 sized to receive corresponding threads of the lower clamping body 206. Note that the clamping bolt 204 may have numerous other shapes and configurations in accordance with the invention.

The lower clamping body 206 is rectangularly-shaped and has a C-shaped profile with a generally rounded lower surface 228 and a generally flat upper surface 230 sized to receive the lower surface 210 of the upper clamping body 202. On a lateral side 232 between the lower surface 228 and upper surface 230, a pair of semi-circular cable channels 234 are machined in the upper surface 230. The cable channels 234 are sized to receive the width of an orthopedic surgical cable (not shown) and are machined through the width of the lower clamping body 206 along the upper surface 230 to the opposing lateral side. Each cable channel 234 includes a series of grooves 236 or ridges machined in the length of the cable channel 234 of the lower clamping body 206. A series of corresponding grooves (not shown) or ridges is also machined in the length of the cable channel 214 of the upper clamping body 202.

Through the upper surface 230, a threaded bolt hole 238 for receiving the clamping bolt 204 is machined through the thickness of the lower clamping body 206 to the lower surface 228. Note that the lower clamping body 206 can have numerous other shapes and configurations in accordance with the invention.

When the threaded bolt hole 236 is concentrically aligned with the bolt hole 216 of the upper clamping body 202, ends 240 of the upper clamping body 202 fit within recesses 242 of the lower clamping body, thus assisting alignment of the semi-circular-shaped cable channels 214 of the upper clamping body 202 with the semi-circular-shaped cable channels 234 of the lower clamping body 206 to form a pair of circular-shaped cable holes for the stand alone-type clamp 200. In this configuration, the series of grooves 236 of the lower clamping body 206 and corresponding grooves (not shown) of the upper clamping body 202 align with each other to decrease the width of the circular hole formed by the alignment of the cable channels 214, 234. Furthermore, when the upper clamping body is aligned with the lower clamping body clamping bolt 204, the clamping bolt 204 can be inserted through the bolt hole 216 and then torqued to engage the threads of the threaded bolt hole 238 of the lower clamping body 206.

A surgical cable clamp such as a stand alone-type clamp 200 can be manufactured from titanium, stainless steel, cobalt chromium alloy, or another similar type of material. An example of a stand alone-type clamp 200 measures approximately 0.3 inches (7.6 mm) in width perpendicular to the orientation of the surgical cable, approximately 0.2 inches (5.1 mm) in height, and approximately 0.5 inches in length (12.7 mm) parallel with the orientation of the surgical cable when the upper clamping body and lower clamping body are aligned together. An example of a clamping bolt is a conventional #8 machine screw made from titanium, stainless steel, cobalt chromium alloy, or a similar type of material that is compatible with material of the upper and lower clamping body. In some instances, the clamping bolt may be coated with an implantable coating designed to reduce frictional contact with other components of the clamp. Furthermore, an example of a surgical cable that can be used with the stand alone-type clamp 200 is typically a cobalt chromium or stainless steel cable measuring approximately 0.04 to 0.08 inches (1.0 to 2.0 mm) in diameter.

The stand alone-type clamp 200 is a preferred embodiment of a surgical cable clamp. The embodiments shown in FIGS. 1b, 1c, 4, and 6-25 are other embodiments of the invention that can also be used in the preferred environment shown in FIG. 1a. Other embodiments of a surgical cable clamp can be used in the preferred environment and other similar type environments to accomplish similar functions in accordance with the invention.

FIGS. 3a-c illustrate a sequence for a method for using the surgical cable clamp shown in FIGS. 1a and 2. The particular embodiment shown in this sequence utilizes a stand alone-type surgical cable clamp, shown in FIG. 2 as 200. Other embodiments of a surgical cable clamp can be utilized with the method illustrated in FIGS. 3a-c.

In FIG. 3a, a surgical cable clamp 300 in accordance with the invention is shown adjacent to an orthopedic device such as a trochanteric grip 302. The trochanteric grip 302 is aligned with a proximal end of a patient's femur bone 304 in accordance with a hip procedure. When the trochanteric grip 302 is to be secured to the patient's femur 304, the surgical cable clamp 300 is positioned in a desired position adjacent to the trochanteric grip 302 to receive an orthopedic surgical cable 306. Typically, the surgical cable clamp 300 is preassembled prior to the sequence. Similar to the cable clamp in FIG. 2, the surgical cable clamp 300 includes an upper clamping body 308, a clamping bolt 310, and a lower clamping body 312, and can be preassembled as described in FIG. 2. A relatively smaller diameter end 314 of a predetermined length of surgical cable 306 is inserted into and pulled through a first cable channel 316 or hole of the surgical cable clamp 300 formed by the assembly and alignment of the upper clamping body 308 with the lower clamping body 312. A bead 318 on a relatively larger diameter end of the surgical cable 306 secures the relatively larger diameter end of surgical cable 308 adjacent to the surgical cable clamp 300 when the length of the surgical cable 306 is pulled through the first cable hole 316.

As shown in FIG. 3b, the relatively smaller diameter end 314 of the surgical cable 306 is inserted through a corresponding cable channel 320 or hole in the trochanteric grip 302 and wrapped around the thickness of the patient's femur 304. When the relatively smaller diameter end 314 of the surgical cable 306 is nearly around the patient's femur 304, the relatively smaller diameter end 314 is inserted through a second cable channel 322 or hole of the surgical cable clamp 300.

As shown in FIG. 3c, the relatively smaller diameter end 314 of the surgical cable 306 is manually pulled through the second cable channel 322 or hole or with a cable tensioning device (not shown) until a desired tension in the surgical cable 306 is attained. When the surgical cable 306 is pulled to a desired tension, the clamping bolt 310 is tightened with a hexagonal-shaped tightening instrument (not shown) until a compression force between the upper clamping body 308 and lower clamping body 312 maintains the desired tension on the surgical cable 306. Any excess length of surgical cable can be trimmed with a cutting instrument (not shown).

In some instances, a cable tensioning device (not shown) can be used to tighten the surgical cable 306 to a predetermined tension. A tightening instrument with a corresponding hexagonal-shaped head or driver such as a "T-handled driver" with a hex head to match the shape of the clamping bolt can then be used to tighten the clamping bolt 310 to a preset torque while measuring the tension on the surgical cable with the cable tensioning device as the clamping bolt 310 is tightened. A suitable cable tensioning device can be a device or system that applies a tension to a surgical cable, maintains the tension on the surgical cable until the tightening instrument can be used to tighten the clamping bolt of the surgical cable clamp, measures the tension in the surgical cable, and releases the surgical cable when the clamping bolt has secured the surgical cable.

More than one surgical cable 306 may be needed to secure an orthopedic device such as a trochanteric grip or bone plate 302 to a patient's femur 304. The above sequence can repeat as needed until the trochanteric grip or other orthopedic device is secured to the patient's femur or bone. After tensioning one or more surgical cables 306 to the patient's femur with one or more corresponding surgical cable clamps 300, previously tensioned surgical cables may tend to loosen or otherwise require additional tension to sufficiently secure the orthopedic device such as a trochanteric grip 302 to the patient's femur 304. If necessary, the tension on a previously tensioned surgical cable can be released by applying an untightening force to the clamping bolt 310 with the hexagonal-shaped tightening instrument, releasing the compression force between the upper clamping body 308 and lower clamping body 312, thus releasing the compression and tension on the surgical cable 306. The surgical cable 306 is then retensioned manually or by use of the cable tensioning device. When the desired tension is reached, a tightening force is applied to the clamping bolt 310 in order to create a sufficient compression force between the upper clamping body 308 and the lower clamping body 312 to maintain the desired tension in the surgical cable 306, and secure the position of the surgical cable 306 relative to the surgical cable clamp 300.

Tensioning and retensioning of one or more surgical cables 306 may occur more than once during a surgical procedure until all of the surgical cables 306 are sufficiently tensioned to maintain the position of the surgical cables 306, bone plate and or trochanteric grip 302 relative to the patient's femur 304. The sequence described above with respect to FIGS. 3a-c can be repeated as necessary to accomplish this.

Preferably, the surgical cable clamp illustrated in FIGS. 3a-c and in other figures can be preassembled prior to installation or use. Preassembly of a surgical cable clamp can include assembling component parts of the surgical cable clamp together with, or without, an orthopedic surgical cable so that a user such as a surgeon can rapidly install or use the surgical cable clamp. In many cases, preassembly of the surgical cable clamp with an orthopedic surgical cable saves time during a surgical procedure when installing or using the surgical cable clamp.

FIGS. 4a-b illustrate another embodiment of a surgical cable clamp in accordance with the invention. FIG. 4a is a perspective view of an embodiment of a device-incorporated clamp 400 similar to that shown as 110 in FIG. 1a; and FIG. 4b illustrates a cross-sectional view of the embodiment shown in FIG. 4a. The embodiment of the device-incorporated clamp 400 shown here includes a device body 402, a clamping bolt 404, and a clamping body 406.

The device body 402 in this embodiment is a bone plate such as a portion of a trochanteric grip with a relatively flat lower surface 408 and a relatively flat upper surface 410. Typically, the lower surface 408 is adjacent to a patient's bone or other structure, while the upper surface 410 remains exposed. On a lateral side 412 of the device body 402, a pair of cable holes 414 sized to receive the ends of an orthopedic surgical cable (not shown) are machined through the width of the device body 402 to the opposing lateral side. Between the lower surface 408 and upper surface 410, a bolt hole 416 for receiving the clamping bolt 404 is machined through the thickness of the device body 402. In the lower surface 408, a recess 418 for receiving a portion of the clamping body 406 is concentrically positioned with the bolt hole 416. Note that the device body 402 can have numerous other shapes and configurations for receiving the clamping body 406 and clamping bolt 404 in accordance with the invention.

The clamping bolt 404 in this embodiment is shaped similar to a conventional machine screw with a socket head 420, a threaded body 422, and blunt point 424. The socket head 420 is sized to receive a hexagonal-shaped tightening instrument (not shown) for tightening and untightening a corresponding socket-shaped head. Alternatively, the external shape of the socket head 420 can be shaped for tightening with a wrench-type instrument (not shown) for tightening and untightening a corresponding geometrically-shaped socket head 420. The threaded body 422 includes one or more threads 426 sized to engage corresponding threads machined in the clamping body 406. The blunt point 424 of the clamping bolt 404 is sized to fit within the bolt hole 416 in the upper surface 410 of the device body 402. Note that the clamping bolt 404 may have numerous other shapes and configurations in accordance with the invention.

The clamping body 406 is shaped like a wingnut, but can also be shaped similar to the upper clamping body shown in FIG. 2. Typically, the clamping body 406 includes a rounded upper surface 428, a generally flat lower surface 430, a pair of semi-circular channels 432 in the lower surface 430, and a bolt hole 434 through the thickness of the clamping body 406 between the upper surface 428 and the lower surface 430. Each channel 432 can include a series of grooves (not shown) or ridges machined in the length of the channel 432 of the clamping body 406. A series of corresponding grooves (not shown) or ridges can also be machined in the length of a corresponding channel (not shown) of the device body 402. The clamping body 406 is sized to fit within the recess 418 in the lower surface 408 of the device body 402. When the clamping body 406 is positioned within the recess 418, the bolt hole 434 of the clamping body 406 is concentric with the threaded bolt hole 416 of the device body 402, thus providing a receiving hole for the clamping bolt 404. Note that the clamping body 406 and corresponding recess 418 can have numerous other shapes and configurations in accordance with the scope of the invention.

A surgical cable clamp such as a device-incorporated clamp 400 can be manufactured from titanium, stainless steel, cobalt chromium alloy, or another similar type of material. An example of a device-incorporated clamp 400 measures approximately 0.3 inches (7.6 mm) across the width of the clamping body perpendicular to the orientation of the surgical cable, and approximately 0.25 inches (6.4 mm) across the diameter of the clamping body perpendicular to the orientation of the surgical cable. An example of a suitable clamping bolt for the device-incorporated clamp is a #8 machine screw made from titanium, stainless steel, cobalt chromium alloy, or a similar type of material that is compatible with material of the device body and clamping body. In some instances, the clamping bolt may be coated with an implantable coating designed to reduce frictional contact with other components of the clamp or device.

The device-incorporated clamp 400 in FIG. 4 is one embodiment of a surgical cable clamp. The embodiment shown in FIG. 4 is an embodiment of the invention that can be used with the structure shown in the preferred environment shown in FIG. 1. Other embodiments of a surgical cable clamp can also be used in the preferred environment and other similar type environments to accomplish similar functions in accordance with the invention.

FIGS. 5a-d illustrate a sequence for a method for using a surgical cable clamp shown in FIGS. 1b and 1c. The particular embodiment shown in this sequence utilizes a device-incorporated clamp, similar to that shown in FIG. 1b as 114 and FIG. 1c as 118. Other embodiments of a surgical cable clamp can be utilized with the method illustrated in FIGS. 5a-d.

As shown in FIG. 5a, a surgical cable clamp 500 is shown incorporated into an orthopedic device such as trochanteric grip 502. The trochanteric grip 502 is aligned with a proximal end of a patient's femur bone 504 in accordance with a hip replacement procedure. When the trochanteric grip 502 is to be secured to the patient's femur 504, the surgical cable clamp 500 is positioned in a position adjacent to the patient's femur 504 to receive a surgical cable 506. Similar to the embodiments shown in FIGS. 1b and 1c, the surgical cable clamp 500 includes a device body, i.e. a portion of the trochanteric grip 502, a clamping bolt 508 and an upper clamping body 510. Typically, the orthopedic device such as a trochanteric grip 502 has an upper surface 512 with a recess 514 sized to receive the upper clamping body 510. The trochanteric grip 502 also has a threaded bolt hole 516 machined through the recess 514 and sized to receive the clamping bolt 508. A relatively smaller diameter end 518 of a predetermined length of surgical cable 506 is inserted into and pulled through a first cable hole 520 in a lateral side of the trochanteric grip 502. A bead 522 on the relatively larger diameter opposing end of the surgical cable 506 secures the opposing end of surgical cable 506 adjacent to the trochanteric grip 502 as shown in FIG. 5b. Preferably, the components of a surgical cable clamp 500 can be preassembled with the orthopedic device prior to the surgical procedure, or otherwise assembled together with the surgical cable 506 during the sequence.

After the surgical cable 506 is wrapped around the thickness of the patient's femur 504, the relatively smaller diameter end 518 of the surgical cable 506 is inserted through a second cable hole 524 of the trochanteric grip 502.

As shown in FIG. 5c, the relatively smaller diameter end 518 and the length of the of the surgical cable 506 is pulled through the second cable hole 524 until a desired tension in the surgical cable 506 is attained. When the surgical cable 506 is pulled to a desired tension, the clamping bolt 508 is mounted through the upper clamping body 510 and tightened into the threaded bolt hole 516 with a tightening instrument (not shown) with a corresponding hexagonal-shaped head or driver such as a "T-handled driver" with a hex head to match the shape of the clamping bolt 508 until the compression force between the upper clamping body 510 and the recess 514 maintains a desired tension on the surgical cable 506. Any excess length of surgical cable 506 can be trimmed with a cutting instrument (not shown).

FIG. 5d illustrates a detailed cutaway cross-sectional view of the surgical cable clamp 500 and trochanteric grip 502 shown in FIGS. 5a-c. As described above and shown here, the upper clamping body 510 is secured to the device body, i.e. a portion of the trochanteric grip 502, with the clamping bolt 508. The position of the surgical cable 506 with respect to the trochanteric grip 502 is maintained by the downward force of the upper clamping body 510 and the clamping bolt 508. A series of corresponding grooves (not shown) or ridges can be machined in the recess 514 of the trochanteric grip 502 adjacent to the position of the surgical cable 506 in order to increase frictional contact on the surgical cable 506.

In most instances, a cable tensioning device (not shown) can be used to tighten the surgical cable 506 to a predetermined tension. The cable tensioning device can be configured to maintain a tension on the surgical cable 506 as well as to measure the tension on the surgical cable 506 until the cable 506 is secured by the clamping bolt 508

More than one surgical cable 506 may be needed to secure an orthopedic device such as a trochanteric grip 502 to a patient's femur 504 or another bone. After tensioning one or more surgical cables 506 to the patient's femur 504 or other bone with one or more corresponding surgical cable clamps 500, previously tensioned surgical cables may tend to loosen or otherwise require additional tension to sufficiently secure the orthopedic device such as a trochanteric grip 502 to the patient's femur 504 or other bone. If necessary, the tension on a previously tensioned surgical cable can be released by applying a force to the clamping bolt 508 with the hexagonal-shaped tightening instrument, releasing the compression force between the upper clamping body 510 and recess 514, thus releasing the tension from the surgical cable 506. The surgical cable 506 is then retensioned manually or by use of the cable tensioning device. When the desired tension is reached, a tightening force is applied to the clamping bolt 508 in order to create a sufficient compression force between the upper clamping body 510 and the recess 514 to maintain the desired tension in the surgical cable 506, and secure the position of the surgical cable 506 relative to the surgical cable clamp 500.

Tensioning and retensioning of one or more surgical cables may occur more than once during a surgical procedure until all of the surgical cables are sufficiently tensioned to maintain the position of the orthopedic device such as a trochanteric grip 502 relative to the patient's femur 504 or other bone. The sequence described above with respect to FIGS. 5a-d can be repeated as necessary to accomplish this.

There are multiple shapes and structures for a surgical cable clamp in accordance with various embodiments of the invention. Without limiting the scope of the invention, the following FIGS. 6-25 are intended to illustrate and describe several embodiments of a surgical cable clamp in accordance with the invention. The surgical cable clamps in each of the embodiments shown in FIGS. 6-25 accomplish similar functions to the embodiments such as the stand alone-type clamp and device-incorporated clamp shown and described above in FIGS. 1-5.

FIG. 6 is a perspective view of another embodiment of a surgical cable clamp 600. The embodiment of the surgical cable clamp 600 shown here includes a clamping body 602, a clamping bolt 604, and a corresponding nut 606.

The clamping body 602 in this embodiment has a generally rounded cap-like configuration with a relatively flat upper surface 608 and a relatively flat lower surface 610. On a circular lateral side 612 of the clamping body 602, a pair of cable holes 614 sized to receive the ends of an orthopedic surgical cable (not shown) are machined through the width of the clamping body 602 to the opposing lateral side. Through the upper surface 608, a bolt hole 616 for receiving the clamping bolt 604 is machined through the thickness of the clamping body 602 to the lower surface 610. A pair of opposing recesses 618 for receiving a portion of the corresponding nut 606 are located on the lateral side 612 of the clamping body 602 opposing one another, and extend from the lower surface 610 towards the upper surface 608. The clamping body 602 includes a concentric nut hole (not shown) in the lower surface 610 sized to receive the width of the corresponding nut 606, and concentrically aligned with the bolt hole 616 through the clamping body 602.

The clamping bolt 604 in this embodiment is shaped similar to a conventional machine screw with a socket head 620, a threaded body 622, and blunt point 624. The socket head 620 is sized to receive a tightening instrument (not shown) for tightening and untightening a corresponding socket-shaped head. Alternatively, the external shape of the socket head 620 can be shaped for tightening with a wrench-type instrument (not shown) for tightening and untightening a corresponding geometrically-shaped socket head 620. The threaded body 622 includes one or more threads 626 sized to receive the corresponding nut 606. The blunt point 624 of the clamping bolt 604 is sized to fit within the bolt hole 616 of the clamping body 602 and to receive the corresponding nut 606.

The corresponding nut 606 is shaped similar to a conventional wingnut with a rounded body 628 and one or more wings 630 extending from opposing lateral sides of the rounded body 628. The rounded body 628 is sized to fit within the concentric nut hole (not shown) in the lower surface 610 of the clamping body 602. A threaded receiving hole 632 is machined through a central portion of the rounded body 630 from an upper side 634 to an opposing lower side 636. Each of the wings 630 is sized to fit within the corresponding opposing recesses 618 in the lateral side 612 of the clamping body 602.

FIG. 7 is an exploded perspective view of another embodiment of a surgical cable clamp similar to that shown in FIG. 6 as 600. The embodiment of the surgical cable clamp 700 shown here includes a clamping body 702, a clamping bolt 704, and a corresponding nut 706, and operates in a similar manner as the embodiment in FIG. 6. The clamping body 702 has a generally rectangular-shaped configuration, while the clamping bolt 704 and associated nut 706 have similar shapes as those shown and described in FIG. 6. The surgical cable clamp 700 shown operates in a substantially similar manner as the clamp shown in FIG. 6 as 600.

FIGS. 8a-b illustrate another embodiment of a surgical cable clamp in accordance with the invention. FIG. 8a shows a cross-sectional view of an embodiment of a surgical cable clamp in an unclamped position, and FIG. 8b shows the clamp of FIG. 8a in a clamped position. This surgical cable clamp 800 includes an upper clamping body 802, a lower clamping body 804, and a clamping bolt 806. Both the upper clamping body 802 and lower clamping body 804 are each generally wedge-shaped. The upper clamping body 802 has an angled surface 808 configured to correspond with a similarly angled surface 810 of the lower clamping body 804 when the clamping bodies are fit together along a relatively flat interface 812. Both the upper clamping body 802 and the lower clamping body each have a corresponding machined bolt hole 814a, 814b through their center portions. The clamping bolt 806 fits within the bolt holes 814a,b when the upper clamping body 802 is aligned with the lower clamping body 804 as shown in FIG. 8a. The clamping bolt 806 may be threaded to correspond with threads of a corresponding nut 816 or with threads machined within the bolt hole 814b of the lower clamping body 804. At least one cable hole 818a is machined in a lateral side 820 of the lower clamping body 804, and a corresponding cable hole 818b is machined in a lateral side 822 of the upper clamping body 802. The cable holes 818a,b are sized to receive an orthopedic surgical cable 824 when the cable holes 818a,b are aligned as shown in FIG. 8a.

When the upper clamping block 802 is slightly offset from the lower clamping block 804 along the interface 812 and the clamping bolt 806 is tightened, then the surgical cable clamp 800 clamps the surgical cable 824 as shown in FIG. 8b. Utilizing this configuration, a user can apply a desired tension to the surgical cable 824, and then clamp the surgical cable 824 by offsetting the upper clamping block 802 from the lower clamping block 804. The compression force of the upper clamping body 802 upon the surgical cable 824 at the interface 812, and the surgical cable 824 against the lower clamping body 804, secures the position of the surgical cable 824 relative to the surgical cable clamp 800. By tightening and untightening the clamping bolt 806 and offsetting or aligning the clamping bodies 802, 804, the surgical cable clamp 800 can clamp and unclamp the orthopedic surgical cable 824.

FIGS. 9a-b illustrate another embodiment of a surgical cable clamp in accordance with the invention. FIG. 9a is a perspective exploded view of a surgical cable clamp; and FIG. 9b is a cross-sectional view of the surgical cable clamp shown in FIG. 9a. In this embodiment, a surgical cable clamp 900 includes an upper clamping body 902, a clamping bolt 904, and a lower clamping body 906. The upper clamping body 902 is generally flat and annularly-shaped, and configured to fit within a corresponding recess 908 in the lower clamping body 906. The lower clamping body 906 is generally block-shaped with the recess 908 machined through a portion of the top surface, and the clamping bolt 904 has a similar shape as the clamping bolt shown and described in FIG. 6. A bolt hole 910 machined through a central portion of the upper clamping body 902 is configured to receive the clamping bolt 904, while a threaded bolt hole 912 is machined in the lower portion of the lower clamping body 906 within the recess 908.

The clamping bolt 904 is threaded to correspond with threads machined within the threaded bolt hole 912. Two cable holes 914 are machined in a lateral side 916 of the lower clamping body 906. The cable holes 914 are sized to receive an orthopedic surgical cable (not shown) to be clamped and reclamped by the surgical cable clamp 900.

When an orthopedic surgical cable is inserted within either or both of the cable holes 914, the upper clamping body 902 can be inserted within the recess 908 of the lower clamping body 906 as shown in FIG. 9b. Then the upper clamping body 902 is secured within the recess 908 by the clamping bolt 904 mounted within the bolt hole 910 and threaded within bolt hole 912. The compression force of the upper clamping body 902 upon the surgical cable secures the position of the surgical cable relative to the lower clamping body 906. By tightening and untightening the clamping bolt 904, the surgical cable clamp 900 can clamp and unclamp the orthopedic surgical cable as needed when tensioning the orthopedic surgical cable as desired. A series of grooves (not shown) or ridges can be machined on the lower surface of the upper clamping body to increase the friction or grip on the surgical cable.

FIGS. 10a-b illustrate another embodiment of a surgical cable clamp in accordance with the invention. FIG. 10a is a perspective exploded view of a surgical cable clamp; and FIG. 10b is a cross-sectional view of the surgical cable clamp shown in FIG. 10a. In this embodiment, a surgical cable clamp 1000 includes a upper clamping body 1002, a lower clamping body 1004, and a clamping bolt 1006. The upper clamping body 1002 is generally C-shaped with a lower recess 1008 sized to receive the generally rectangular-shaped lower clamping body 1004. When fit together, the lower clamping body 1004 integrally fits with the upper clamping body 1002 as shown in FIG. 10b. The clamping bolt 1006 fits within a bolt hole 1010 machined through the central portion of the upper clamping body 1002, and has a similar shape as the clamping bolt shown and described in FIG. 6. A threaded bolt hole 1012 machined in the lower clamping body 1004 is sized to receive threads of the clamping bolt 1006. Two cable channels 1014 are machined in the lower portion of a lateral side 1016 of the upper clamping body 1002. These cable channels 1014 correspond with cable channels 1018 machined in an upper portion of the lower clamping body 1004. When the upper clamping body 1002 and lower clamping body 1004 are integrally fit together, the cable channels 1014, 1018 align with each other. The cable channels 1014, 1018 are sized to receive an orthopedic surgical cable (not shown) to be clamped and reclamped by the surgical cable clamp 1000. A series of grooves (not shown) or ridges can be machined within the cable channels 1014, 1018 to increase the friction or grip on the surgical cable.

When an orthopedic surgical cable is inserted within either or both of the cable holes, the upper clamping body 1002 is fit together with the lower clamping body 1004, and then the upper clamping body 1002 is secured to the lower clamping body 1004 by the clamping bolt 1006. The compression force of the upper clamping body 1002 upon the surgical cable secures the position of the cable relative to the lower clamping body 1004. By tightening and untightening the clamping bolt 1006, the surgical cable clamp 1000 can clamp and unclamp the orthopedic surgical cable as needed when tensioning the orthopedic surgical cable as desired.

FIGS. 11a-b illustrate another embodiment of a surgical cable clamp in accordance with the invention. FIG. 11a is a perspective exploded view of a surgical cable clamp; and FIG. 11b is a cross-sectional view showing clamp position of the surgical cable clamp shown in FIG. 11a. The embodiment of a surgical cable clamp 1100 shown here includes a clamping body 1102, a clamping bolt 1104, and a corresponding nut 1106, and operates in a similar manner as the embodiment in FIG. 6. The clamping body 1102 has a generally block-shaped configuration with a recess 1108 in the lower surface, while the clamping bolt 1104 has a similar shape as the clamping bolt shown and described in FIG. 6. The corresponding nut 1106 is annular shaped with a wedge-shaped cross-section, configured to fit within the circular-shaped recess 1108 in the clamping body 1102. A bolt hole 1110 machined through the central portion of the clamping body 1102 corresponds with a threaded bolt hole 1112 in the corresponding nut 1106. When the clamping body 1102 and the corresponding nut 1106 are aligned, the clamping bolt mounts through the bolt hole 1110 and threads into the threaded bolt hole 1112 of the corresponding nut 1106. Two cable holes 1114 are machined in a lateral side 1116 of the clamping body 1102. Each cable hole 1114 extends along a portion of the lateral edge of the recess 1108 within the clamping body 1102, and through to the opposing lateral side of the clamping body 1102.

When an orthopedic surgical cable is inserted within either or both the cable holes 1114, the clamping body 1102 can then be fit together with the corresponding nut 1106. The corresponding nut 1106 is secured to the clamping body 1102 by the clamping bolt 1104. The compression force of the corresponding nut 1106 upon the surgical cable secures the position of the cable relative to the clamping body 1102. By tightening and untightening the clamping bolt 1104, the surgical cable clamp 1100 can clamp and unclamp the orthopedic surgical cable as needed when tensioning the orthopedic surgical cable as desired.

FIGS. 12a-b illustrate another embodiment of a surgical cable clamp in accordance with the invention. FIG. 12a is a side view of the surgical cable clamp in an unclamped position, and FIG. 12b is a side view of the surgical cable clamp in FIG. 12a in a clamped position. In this embodiment, a surgical cable clamp 1200 includes a upper clamping body 1202, a lower clamping body 1204, and a spring 1206. The upper clamping body 1202 is configured to hingably fit together with the lower clamping body 1204 via a hinge 1208. Together, the upper clamping body 1202 connected to the lower clamping body 1204 form a C-shaped device. A cable support 1210 connects to the upper clamping body 1202, while a corresponding cable support 1212 connects to the lower clamping body 1204. Each of the cable supports 1210, 1212 is eye bolt-shaped. When the clamp 1200 is in an unclamped position as shown in FIG. 12a, the cable supports 1210, 1212 align with each other, as well as with a cable hole 1214 adjacent to the hinge 1208 and between adjacent ends of the upper clamping body 1202 and lower clamping body 1204.

The spring 1206 mounts between and connects the upper clamping body 1202 and lower clamping body 1204, adjacent to the hinge 1208. When the clamp 1200 is in a clamped position as shown in FIG. 12b, the spring 1206 maintains the upper clamping body 1202 and lower clamping body 1204 in a spaced apart relation that offsets the alignment of the cable supports 1210, 1212. For example, when an orthopedic surgical cable 1216 is mounted through the cable hole 1214 and through each of the aligned cable supports 1210, 1212 as shown in FIG. 12a, the surgical cable clamp 1200 does not provide any clamping force upon the cable 1216. However, as shown in FIG. 12b, when the upper clamping body 1202 and lower clamping body 1204 are extended away from each other, the offset alignment of the cable supports 1210, 1212 causes the surgical cable clamp 1200 to slightly offset or "clamp" the cable 1216, thus securing the position of the surgical cable 1216 relative to the surgical cable clamp 1200. By compressing or extending the upper and lower clamping bodies 1202, 1204 together or away from each other, the surgical cable clamp 1200 can clamp and unclamp the orthopedic surgical cable 1216 as needed when tensioning the orthopedic surgical cable 1216 as desired.

FIGS. 13a-b illustrate another embodiment of a surgical cable clamp in accordance with the invention. FIG. 13a is a cross-sectional view of the surgical cable clamp in a clamped position, and FIG. 13b is an exploded side view of the surgical cable clamp in FIG. 13a in an unclamped position. In this embodiment, a surgical cable clamp 1300 includes a upper clamping body 1302, a lower clamping body 1304, and a pair of clamping bolts 1306. The wedge-shaped upper clamping body 1302 is configured to integrally fit within a corresponding recess 1308 of the lower clamping body 1304. Together, the upper clamping body 1302 and lower clamping body 1304 form a general block-shape. The clamping bolts 1306 each have a similar shape as the clamping bolt shown and described in FIG. 6. A set of bolt holes 1310 in the upper clamping body 1302 correspond with threaded bolt holes 1312 in the lower clamping body 1304. Each of the bolt holes 1310, 1312 is sized to receive the clamping bolts 1306.

At least one cable hole 1314 is machined in a lateral side 1316 of the lower clamping body 1304. At an interface between the upper clamping body 1302 and lower clamping body 1304, a second cable hole 1318 is formed when the upper clamping body 1302 fits together with the lower clamping body 1304. For example, a tip portion 1320 of the upper clamping body 1302 can be a concave-shaped tip, and the recessed portion 1322 of the lower clamping body 1304 can be a concave-shaped recess that corresponds to the tip portion of the upper clamping body 1302 to form a second cable hole 1318. The cable hole 1310 and second cable hole 1318 are sized to receive an orthopedic surgical cable (not shown) to be clamped and reclamped by the surgical cable clamp 1300.

When an orthopedic surgical cable is inserted within either or both the cable hole 1310 and second cable hole 1318, the upper clamping body 1302 can then be secured together with the lower clamping body 1304 by the clamping bolts 1306. The compression force of the upper clamping body 1302 upon the surgical cable secures the position of the cable relative to the lower clamping body 1304. By tightening and untightening the clamping bolts 1306, the surgical cable clamp can clamp and unclamp the orthopedic surgical cable as needed when tensioning the orthopedic surgical cable as desired. A series of grooves (not shown) or ridges to increase the friction or grip on the surgical cable can be machined within the second cable hole 1318 by machining the upper clamping body 1302 and/or lower clamping body 1304.

FIGS. 14a-b show another embodiment of a surgical cable clamp in accordance with the invention. FIG. 14a is a side view of the surgical cable clamp in a clamped position, and FIG. 14b is a side view of the surgical cable clamp in FIG. 14a in an unclamped position. In this embodiment, a surgical cable clamp 1400 includes an upper clamping body 1402, a lower clamping body 1404, and a clamping bolt 1406. The upper clamping body 1402 is configured to hingably fit together with the lower clamping body 1404 via a hinge 1408. Together, the upper clamping body 1402 and lower clamping body 1404 form a V-shape. A bolt hole 1410 in the upper clamping body 1402 adjacent to an unhinged end corresponds with a threaded bolt hole 1412 in the lower clamping body 1404 adjacent to its unhinged end. Each of the bolt holes 1410, 1412 are sized to receive the clamping bolt 1406. The clamping bolt 1406 has a similar shape as the clamping bolt shown and described in FIG. 6.

At least one cable hole 1414 is machined in a lateral side 1416 of the upper clamping body 1402. At an interface between the upper clamping body 1402 and lower clamping body 1404, a second cable hole 1418 is formed when the upper clamping body 1402 fits together with the lower clamping body 1404. For example, a recessed portion 1420 of the upper clamping body 1402 can be a concave-shaped cable channel, and a recessed portion 1422 of the lower clamping body 1404 can be a concave-shaped cable channel that corresponds to the recessed portion 1420 of the upper clamping body 1402 to form a second cable hole 1418. The cable hole 1410 and second cable hole 1418 are sized to receive an orthopedic surgical cable (not shown) to be clamped and reclamped by the surgical cable clamp 1400.

When an orthopedic surgical cable is inserted within either or both the cable hole 1410 and second cable hole 1418, the upper clamping body 1402 can then be secured together with the lower clamping body 1404 by the clamping bolt 1406. The compression force of the upper clamping body 1402 upon the surgical cable secures the position of the cable relative to the lower clamping body 1404. By tightening and untightening the clamping bolt 1406, the surgical cable clamp 1400 can clamp and unclamp the orthopedic surgical cable as needed when tensioning the orthopedic surgical cable as desired. A series of grooves (not shown) or ridges to increase the friction or grip on the surgical cable can be machined within the second cable hole 1418 by machining the upper clamping body 1402 and/or lower clamping body 1404.

FIGS. 15a-b illustrate another embodiment of a surgical cable clamp in accordance with the invention. FIG. 15a is a cross-sectional view of the surgical cable clamp in a clamped position, and FIG. 15b is an exploded side view of the surgical cable clamp in FIG. 15a in an unclamped position. In this embodiment, a surgical cable clamp 1500 includes an upper clamping body 1502, a lower clamping body 1504, and a pair of clamping bolts 1506. The lower clamping body 1504 forms an inverted T-shape and integrally fits within a corresponding recess 1508 in the lower portion of the upper clamping body 1502. The clamping bolts 1506 fit within a pair of respective bolt holes 1510 machined through portions of the upper clamping body 1502 and within corresponding threaded bolt holes 1512 machined in the lower clamping body 1504. Note that the clamping bolts 1506 each have a similar shape as the clamping bolt shown and described in FIG. 6. At least one cable hole 1514 is machined in a lateral side 1516 of the upper clamping body 1502. A second cable hole 1518 is formed when the upper clamping body 1502 is fit together with the lower clamping body 1504. For example, a tip portion 1520 of the T-shaped lower clamping body 1504 can have a concave-shaped tip and a corresponding recessed portion 1522 in the upper clamping body 1502 can be a concave-shaped portion that forms a second cable hole 1518 when the upper clamping body 1502 is integrally fit together with the lower clamping body 1504. The cable hole 1510 and second cable hole 1518 are sized to receive an orthopedic surgical cable (not shown) to be clamped and reclamped by the surgical cable clamp 1500.

One or more springs 1524 may be positioned between the upper clamping body 1502 and the lower clamping body 1504 to assist with the disassembly of the upper clamping body 1502 from the lower clamping body 1504. In the example shown, the springs 1524 are concentrically positioned around the clamping bolts 1506, and are configured to compress when the lower clamping body 1502 is compressed within the recess 1508 of the upper clamping body as shown in FIG. 15a.

When an orthopedic surgical cable is inserted within either or both the cable hole 1510 and second cable hole 1518, the lower clamping body 1504 can then be fit together with the upper clamping body 1502, and then the lower clamping body 1504 is secured to the upper clamping body 1502 by the clamping bolts 1506. The compression force of the lower clamping body 1504 upon the surgical cable secures the position of the cable relative to the upper clamping body 1502. By tightening and untightening either or both of the clamping bolts 1506, the surgical cable clamp 1500 can clamp and unclamp the orthopedic surgical cable as needed when tensioning the orthopedic surgical cable as desired. A series of grooves (not shown) or ridges to increase the friction or grip on the surgical cable can be machined within the second cable hole 1518 by machining the upper clamping body 1502 and/or lower clamping body 1504.

FIGS. 16a-b show another embodiment of a surgical cable clamp in accordance with the invention. FIG. 16a is a cross-sectional view of the surgical cable clamp in a clamped position, and FIG. 16b is a isometric or perspective view of the surgical cable clamp in FIG. 16a in an unclamped position. In this embodiment, a surgical cable clamp 1600 includes an upper clamping body 1602, a lower clamping body 1604, and a clamping bolt 1606. The cone-shaped lower clamping body 1604 is configured to integrally fit within a corresponding recess 1608 machined in the lower portion of the upper clamping body 1602. The clamping bolt 1606 fits within a bolt hole 1610 machined through a central portion of the upper clamping body 1602, and within a threaded bolt hole 1612 machined in a central portion of the lower clamping body 1604. Note that the clamping bolt 1606 has a similar shape as the clamping bolt shown and described in FIG. 6. At an interface between the lateral sides 1614 of the lower clamping body 1604 and the lateral sides 1616 of the recess 1608, cable clamping areas 1618 are formed when the lower clamping body 1604 is integrally fit within the recess 1608 of the upper clamping body 1602. For example, the lateral sides 1616 of the recess 1608 can each have a pair of concave-shaped recessed portions that are adjacent to the lower clamping body 1604, when the lower clamping body 1604 is fit into the recess 1608. The cable clamping areas 1618 are sized to receive an orthopedic surgical cable (not shown) to be clamped and reclamped by the surgical cable clamp 1600. Thus, when the lower clamping body 1604 is drawn upwards and into the recess 1608 of the upper clamping body 1602, the cable clamping areas 1618 are restricted by the lateral sides 1614 of the lower clamping body 1604.

Cable holes 1620 machined in a lateral side 1622 of the upper clamping body 1602 and through to the opposing later side further align with the cable clamping areas 1618 to permit an orthopedic surgical cable (not shown) to mount through the upper clamping body 1602. When an orthopedic surgical cable is inserted into either or both cable holes 1620 and within either or both corresponding cable clamping areas 1618, the lower clamping body 1604 can then be secured to the upper clamping body 1602 by the clamping bolt 1606. The compression force of the lower clamping body 1604 upon the surgical cable secures the position of the cable relative to the upper clamping body 1602. By tightening and untightening the clamping bolt 1606, the surgical cable clamp 1600 can clamp and unclamp the orthopedic surgical cable as needed when tensioning the orthopedic surgical cable as desired. A series of grooves (not shown) or ridges to increase the friction or grip on the surgical cable can be machined within the along the lateral sides of the lower clamping body 1604 adjacent to the cable clamping areas 1618.

FIGS. 17a-b illustrate another embodiment of a surgical cable clamp in accordance with the invention. FIG. 17a is a cross-sectional view of the surgical cable clamp in a clamped position, and FIG. 17b is an isometric view or perspective view of the surgical cable clamp in FIG. 17a. In this embodiment, a surgical cable clamp 1700 includes a upper clamping body 1702, a lower clamping body 1704, and a clamping bolt 1706. The lower clamping body 1702 is a tapered wedge-shape configured to integrally fit within a corresponding recess 1708 machined in the lower portion of the upper clamping body 1704. The clamping bolt 1706 mounts through a bolt hole 1710 machined through a central portion of the upper clamping body 1702, and within a threaded bolt hole 1712 machined in the lower clamping body 1704. The clamping bolt 1706 may be threaded to correspond with threads machined within bolt hole 1712. Note that the clamping bolt 1706 has a similar shape as the clamping bolt shown and described in FIG. 6. Two cable holes 1714 are machined in a lateral side 1716 of the lower clamping body 1704. At an interface between the upper clamping body 1702 and lower clamping body 1704, a cable clamping area 1718 is formed when the lower clamping body 1704 is integrally fit together with the upper clamping body 1702. At least one of the cable holes 1714 aligns with the cable clamping area 1718. The cable clamping area 1718 is sized to receive an orthopedic surgical cable to be clamped and reclamped by the surgical cable clamp 1700. Thus, when the lower clamping body is drawn upwards and into the recess of the upper clamping body, the cable clamping area 1718 is further restricted by the lower clamping body 1704.

At least one ball spring 1720 is connected to the lower clamping body 1704 and configured to extend between the upper clamping body 1702 and the lower clamping body 1704. The ball spring 1720 assists with the assembly of the lower clamping body 1704 with the upper clamping body 1702. When the surgical cable clamp 1700 is assembled as shown in FIG. 17a, the ball spring 1720 compresses when the lower clamping body 1704 is initially drawn upward within the recess 1708 of the upper clamping body 1702. Conversely, the ball spring 1720 extends into a corresponding ball recess 1722 machined in an opposing lateral side 1724 of the recess 1708 when a predetermined position is reached by the lower clamping body 1704 with respect to the upper clamping body 1702. When the predetermined position is attained, the ball spring 1720 provides a physical stop preventing an undesired release of cable tension caused by the clamping bolt 1706 possibly backing out while in use.

When an orthopedic surgical cable 1726 is inserted within either or both cable clamping areas, the lower clamping body 1704 can then be secured to the upper clamping body 1702 by the clamping bolt 1706. The compression force of the lower clamping body 1704 upon the surgical cable 1726 secures the position of the cable 1726 relative to the upper clamping body 1702. By tightening and untightening the clamping bolt 1706, the surgical cable clamp 1700 can clamp and unclamp the orthopedic surgical cable 1726 as needed when tensioning the orthopedic surgical cable 1726 as desired.

FIGS. 18a-b show another embodiment of a surgical cable clamp in accordance with the invention. FIG. 18a is an exploded isometric view of the surgical cable clamp in an unclamped position, and FIG. 18b is a cross-sectional view showing the clamp position of the surgical cable clamp in FIG. 18a. In this embodiment, a surgical cable clamp 1800 includes a clamping body 1802 and a collet 1804. The clamping body 1802 is configured to fit together with the collet 1804 so that the collet 1804 compresses a portion of the clamping body 1802. The clamping body 1802 includes a pair of extended legs 1806a,b. A cable clamping area 1808 is formed between the extended legs 1806a,b, while opposing cable channels 1810 are machined on the interior lateral sides of each leg 1806a,b. The cable channels 1810 and cable clamping areas 1808 are sized to receive the diameter of an orthopedic surgical cable to be clamped and reclamped by the surgical cable clamp 1800. A cable hole 1812 machined through the clamping body 1802 is also sized to receive the diameter of an orthopedic surgical cable to be clamped and reclamped by the surgical cable clamp 1800.

When an orthopedic surgical cable is inserted within the cable clamping area 1808 and within the cable channels 1810, the extended legs 1806a,b can then be compressed towards each other with the collet 1804. The compression force of the collet 1804 upon the extended legs 1806*a,b* applies a compression force on the surgical cable, thus securing the position of the cable relative to the clamping body 1802. By tightening and untightening the collet 1804, the surgical cable clamp 1800 can clamp and unclamp the orthopedic surgical cable as needed to secure or unsecure the tension in the cable as desired. A series of grooves (not shown) or ridges to increase the friction or grip on the surgical cable can be machined within the cable channels 1810 by machining the interior lateral sides of each leg 1806*a,b*. Other configurations of sizes and shapes for a collet 1804 or similar shaped body or device can be used in accordance with the invention.

FIGS. 19*a-b* show another embodiment of a surgical cable clamp in accordance with the invention. FIG. 19*a* is an exploded isometric view of the surgical cable clamp in an unclamped position, and FIG. 19*b* is a cross-sectional view showing the clamp position of the surgical cable clamp in FIG. 19*a*. In this embodiment, which is similar to the embodiment shown in FIG. 18, a surgical cable clamp 1900 includes a clamping body 1902 and a collet 1904. However, in this embodiment, the collet 1904 is configured to thread onto the clamping body 1902, rather than a slip fit, so that the collet 1904 compresses a portion of the clamping body 1902. The clamping body 1902 includes a pair of extended legs 1906*a,b*. A cable clamping area 1908 is formed between the extended legs 1906*a,b*, while opposing cable channels 1910 are machined on the interior lateral sides of each leg 1906*a,b*. The cable channels 1910 and cable clamping area 1908 are sized to receive the diameter of an orthopedic surgical cable to be clamped and reclamped by the surgical cable clamp 1900. A cable hole 1912 machined through the clamping body 1902 is also sized to receive the diameter of an orthopedic surgical cable to be clamped and reclamped by the surgical cable clamp 1900.

When an orthopedic surgical cable is inserted within the cable clamping area 1908 and within the cable channels 1910, the extended legs 1906*a,b* can then be compressed towards each other with the collet 1904. The compression force of the collet 1904 upon the extended legs 1906*a,b* applies a compression force on the surgical cable, thus securing the position of the cable relative to the clamping body 1902. By tightening and untightening the collet 1904, the surgical cable clamp 1900 can clamp and unclamp the orthopedic surgical cable as needed when tensioning the orthopedic surgical cable as desired. A series of grooves (not shown) or ridges to increase the friction or grip on the surgical cable can be machined within the cable channels 1910 by machining the interior sides of each leg 1906*a,b*.

Note that the collet 1904 can be a cylindrically-shaped compression piece sized to fit on the ends of the extended legs 1906*a,b*. Alternatively, the collet 1904 can be a cylindrically-shaped threaded piece with corresponding threads configured on the exterior of the extended legs 1906*a,b* to receive the threaded collet 1904. Other configurations of sizes and shapes for a collet 1904 or similar shaped body or device can be used in accordance with the invention.

FIG. 20*a* is another embodiment of a surgical cable clamp in accordance with the invention. FIG. 20*a* is a perspective exploded view of a surgical cable clamp in an unclamped position; and FIG. 20*b* is a cross-sectional view showing the clamp position of the surgical cable clamp shown in FIG. 20*a*. In this embodiment, a surgical cable clamp 2000 includes a upper clamping body 2002, a lower clamping body 2004, and a clamping bolt 2006. The upper clamping body 2002 is generally disc-shaped with a pair of cable channels 2008 machined in along the lower portion and sized to receive a diameter of an orthopedic surgical cable 2010 to be clamped and reclamped by the surgical cable clamp 2000. The lower clamping body 2004 is also generally disc-shaped and integrally fits with the upper clamping body 2002 as shown in FIG. 20*b*. The clamping bolt 2006 fits within a bolt hole 2012 machined through the central portion of the upper clamping body 2002, and has a similar shape as the clamping bolt shown and described in FIG. 6. A threaded bolt hole 2014 machined in the lower clamping body 1004 is sized to receive threads of the clamping bolt 2006.

When an orthopedic surgical cable is inserted between the upper clamping body 2002 and the lower clamping body 2004, and within at least one cable channel 2008, then the upper clamping body 2002 can be secured to the lower clamping body 2004 by the clamping bolt 2006. The compression force of the upper clamping body 2002 upon the surgical cable 2010 secures the position of the cable 2010 relative to the lower clamping body 2004. By tightening and untightening the clamping bolt 2006, the surgical cable clamp 2000 can clamp and unclamp the orthopedic surgical cable 2010 as needed when tensioning the orthopedic surgical cable 2010 as desired. A series of grooves (not shown) or ridges can be machined within the cable channels 2008 and/or along the opposing side of the lower clamping body 2004 to increase the friction or grip on the surgical cable.

FIGS. 21*a-b* is another embodiment of a surgical cable clamp in accordance with the invention. FIG. 21 illustrates a perspective view of a surgical cable clamp in a clamped position; and FIG. 21*b* illustrates a cross-sectional view showing the clamp position of the surgical cable clamp shown in FIG. 21*a* also in a clamped position. In this embodiment, a surgical cable clamp 2100 includes a upper clamping body 2102, a lower clamping body 2104, and a clamping bolt 2106. The upper clamping body 2102 is generally wedge-shaped. The lower clamping body 2104 is generally disc-shaped with a corresponding wedge-shaped taper between an upper surface 2108 and lateral surface 2110 of the body 2104. The upper clamping body 2102 integrally fits with the lower clamping body 2104 as shown in FIG. 21*b*. The clamping bolt 2106 fits within a bolt hole 2112 machined through the central portion of the upper clamping body 2102, and has a similar shape as the clamping bolt shown and described in FIG. 6. A threaded bolt hole 2114 machined in the tapered portion of the lower clamping body 1004 is sized to receive threads of the clamping bolt 2006.

A cable hole 2116 and a cable channel 2118 are machined through the lateral side 2110 of the lower clamping body 2104, and each is sized to receive a diameter of an orthopedic surgical cable 2120 to be clamped and reclamped by the surgical cable clamp 2100. The cable channel 2118 is machined along the tapered portion of the lower clamping body 2104, permitting the upper clamping body 2102 to contact a portion of the surgical cable 2120 when the cable 2120 is mounted within the cable channel 2118.

When an orthopedic surgical cable is inserted between the upper clamping body 2102 and the lower clamping body 2104, and within the cable channel 2118, then the upper clamping body 2102 can be secured to the lower clamping body 2104 by the clamping bolt 2106. The compression force of the upper clamping body 2102 upon the surgical cable 2120 secures the position of the cable 2120 relative to the lower clamping body 2104. By tightening and untightening the clamping bolt 2106, the surgical cable clamp 2100 can clamp and unclamp the orthopedic surgical cable 2120 as needed when tensioning the orthopedic surgical cable 2120 as desired. A series of grooves (not shown) or ridges can be machined within the cable channel 2118 and/or along the opposing side of the upper clamping body 2102 to increase the friction or grip on the surgical cable.

FIGS. 22*a-b* are another embodiment of a surgical cable clamp in accordance with the invention. FIG. 22*a* illustrates a cross-sectional view of a surgical cable clamp in an unclamped position; and FIG. 22*b* illustrates a cross-sectional view showing the clamp position of the surgical cable clamp shown in FIG. 22*a*. In this embodiment, a surgical cable clamp 2200 includes a upper clamping body 2202 and a lower clamping body 2204. The upper clamping body 2202 is generally a cylindrically-shaped tube with slotted lateral sides 2206. The lower clamping body 2204 is generally spherically-shaped with slots 2208 in its lateral sides 2210 that correspond with slots 2212 in the upper clamping body 2202. The upper clamping body 2202 integrally fits with the lower clamping body 2204 as shown in FIGS. 22*a-b*. Conventional material joining methods and processes can be used to fit the upper clamping body 2202 with the lower clamping body 2204, or alternatively, the bodies 2202, 2204 can be molded or otherwise formed from a single piece or material.

A cable hole 2214 is machined through the lower clamping body 2204 to receive a diameter of an orthopedic surgical cable 2216 to be clamped and reclamped by the surgical cable clamp 2200. A cable channel 2218 in the upper clamping body 2202 is aligned with the cable hole 2214, and is also configured to receive a diameter of an orthopedic surgical cable 2216. The cable channel 2218 permits the upper clamping body 2202 to contact a portion of the surgical cable 2216 when the cable 2216 is mounted within the cable channel 2218.

When an orthopedic surgical cable is inserted within the cable hole 2214 and mounted within the cable channel 2218, the cable clamp 2200 can be inserted into a cavity 2220 of an orthopedic device 2222 as shown in FIG. 22*a*. This movement causes a compression force to be applied to the exterior of the lower clamping body 2204 causing the lateral sides 2206 of the upper clamping body 2202 to move inward towards the surgical cable 2216 as shown in FIG. 22*b*. The compression force of the upper clamping body 2202 upon the surgical cable 2216 secures the position of the cable 2216 relative to the lower clamping body 2204. When a user inserts or removes the lower clamping body from the cavity 2220, the surgical cable clamp 2200 clamps or unclamps the orthopedic surgical cable 2216 as needed when tensioning the orthopedic surgical cable 2216 as desired. A series of grooves (not shown) or ridges can be machined within the cable channel 2218 and/or along the opposing sides of the upper clamping body 2202 to increase the friction or grip on the surgical cable.

FIGS. 23*a-b* are another embodiment of a surgical cable clamp in accordance with the invention. FIG. 23*a* illustrates a cross-sectional view of a surgical cable clamp in an unclamped position; and FIG. 23*b* illustrates a cross-sectional view showing the clamp position of the surgical cable clamp shown in FIG. 23*a*. In this embodiment, a surgical cable clamp 2300 includes a clamping body 2302. The clamping body of this embodiment is a single molded or manufactured piece, but could be fabricated in multiple pieces similar to the embodiment shown in FIG. 22. The clamping body 2302 is generally a wedge-shaped tube with slotted lateral sides 2304. A cable hole 2306 is machined through the clamping body 2302 to receive a diameter of an orthopedic surgical cable 2308 to be clamped and reclamped by the surgical cable clamp 2300. The cable hole 2306 permits the clamping body 2302 to contact a portion of the surgical cable 2308 when the cable 2308 is mounted within the cable hole 2306.

When an orthopedic surgical cable 2308 is inserted within the cable hole 2306, the cable clamp 2300 can be inserted into a cavity 2310 of an orthopedic device 2312 as shown in FIG. 23*a*. This movement causes a compression force to be applied to the exterior of the clamping body 2302 causing the lateral sides 2304 of the clamping body 2302 to move inward towards the surgical cable 2308 as shown in FIG. 23*b*. The compression force of the clamping body 2302 upon the surgical cable 2308 secures the position of the cable 2308 relative to the clamping body 2302. When a user inserts or removes the lower clamping body from the cavity 2310, the surgical cable clamp 2300 clamps or unclamps the orthopedic surgical cable 2308 as needed when tensioning the orthopedic surgical cable 2308 as desired. A series of grooves (not shown) or ridges can be machined within the cable hole 2306 and/or along the opposing sides of the upper clamping body 2302 to increase the friction or grip on the surgical cable.

FIGS. 24*a-b* illustrate another embodiment of a surgical cable clamp in accordance with the invention. FIG. 24*a* shows a perspective view of a surgical cable clamp, and FIG. 24*b* shows a cross-sectional view of the surgical cable clamp shown in FIG. 24*a*. In this embodiment, a surgical cable clamp 2400 includes a clamping body 2402, and a clamping mechanism 2404. The clamping body 2402 is geometrically shaped with at least one clamping cable hole 2406 machined through the thickness of the body 2402. The clamping cable hole 2406 shown includes a machined out portion 2408 that permits the size of the corresponding clamping cable hole 2406 to be slightly reduced when the clamping body 2402 is compressed. In the configuration shown, the clamping body 2402 has an upper portion 2410 and a lower portion 2412 adjacent to the machined out portion 2408 of the cable hole 2406. The clamping mechanism 2404 is a C-shaped ring that fits within a ridge 2414 that is machined partially around the exterior sides of the upper portion 2410 and lower portion 2412 of the clamping body 2402.

The clamping cable hole 2406 is sized to receive a diameter of an orthopedic surgical cable 2416 to be clamped and reclamped by the surgical cable clamp 2400. When the upper portion 2410 of the clamping body 2402 is compressed towards the lower portion 2412 of the clamping body, the cable hole 2406 compresses slightly to contact a portion of the surgical cable 2416 when the cable 2416 is mounted within the cable hole 2406.

When an orthopedic surgical cable 2416 is inserted between the upper portion 2410 of the clamping body 2402 and the lower portion 2412 of the clamping body 2104, and within the clamping cable hole 2406, then the upper portion 2410 can be secured with respect to the lower clamping body 2412 by positioning the clamping mechanism 2404 within the ridge 2414 and activating the clamping mechanism 2404. The compression force of the clamping mechanism 2404 upon the upper 2410 and lower portions 2412 of the clamping body 2402 compresses the interior sides of the cable hole 2406 upon the surgical cable 2416, while securing the position of the cable 2416 relative to the clamping body 2402. By tightening and untightening the clamping mechanism 2404, the surgical cable clamp 2400 can clamp and unclamp the orthopedic surgical cable 2416 as needed when tensioning the orthopedic surgical cable 2416 as desired. A series of grooves (not shown) or ridges can be machined within the cable hole 2406 to increase the friction or grip on the surgical cable.

Note that the clamping mechanism 2404 can be a material having elastic-like or shape-memory properties, such as nitinol, a memory metal, a material activated by temperature change or heat, a material activated by a force, a material activated by an electrical current, or a material activated by a magnetic force. Other metals, plastics, alloys, composites, or other materials can be used within a clamping mechanism to provide the desired effects. When activated or otherwise in use, the clamping mechanism 2404 is designed to apply a compression force to the clamping body 2402. In the configuration shown in FIGS. 24*a-b*, the clamping mechanism 2404 compresses the upper 2410 and lower portions 2412 of the clamping body 2402 towards each other, reducing the diameter of the cable hole 2406 and clamping a surgical cable within the cable hole 2406. When the clamping mechanism 2404 is deactivated or otherwise not in use, the clamping mechanism 2404 does not apply a compression force to the clamping body 2402, and the diameter of the cable hole 2406 returns to a normal, unreduced size or position.

FIGS. 25a-b illustrate another embodiment of a surgical cable clamp in accordance with the invention. FIG. 25a is a perspective exploded view of a surgical cable clamp; and FIG. 25b is a cross-sectional view of the surgical cable clamp shown in FIG. 25a. The embodiment of a surgical cable clamp 2500 shown here includes a clamping body 2502, and a clamping mechanism 2504. The clamping body 2502 has a generally block-shaped configuration with a circular-shaped recess 2506 in the upper surface, while the clamping nut 2504 is disc shaped to correspondingly fit within the recess 2506 of the clamping body 2502. Typically, the clamping mechanism 2504 is threaded to fit corresponding threads machined in the lateral sides 2508 of the recess 2506. When the clamping body 2502 and the clamping mechanism 2504 are aligned, the clamping mechanism 2504 mounts to the clamping body 2502 with preferably a quarter radial turn of the clamping mechanism 2504 with respect to the clamping body 2502. Other embodiments can provide additional or less threading to secure the clamping mechanism 2504 to the clamping body 2502 using less than or greater than a quarter radial turn. One or more cable holes 2510 are machined in a lateral side 2512 of the clamping body 2502. Each cable hole 2510 extends along and through a portion of the recess 2506 within the clamping body 2502, and through to the opposing lateral side of the clamping body 2502.

When an orthopedic surgical cable 2514 is inserted within the cable hole 2510 as shown, the clamping body 2502 can then be fit together with the clamping mechanism 2504. The clamping mechanism 2504 is secured to the clamping body 2502 by threading the clamping mechanism 2504 into the recess 2506. The compression force of the clamping mechanism 2504 upon the surgical cable 2514 secures the position of the cable 2514 relative to the clamping body 2502. By tightening and untightening the clamping mechanism 2504, the surgical cable clamp 2500 can clamp and unclamp the orthopedic surgical cable 2514 as needed when tensioning the orthopedic surgical cable as desired. A series of grooves (not shown) or ridges can be machined along and within the cable hole 2510 and/or the opposing side of the clamping mechanism 2504 to increase the friction or grip on the surgical cable.

While the above description contains many specifics, these specifics should not be construed as limitations on the scope of the invention, but merely as exemplifications of the disclosed embodiments. Those skilled in the art will envision many other possible variations that within the scope of the invention as defined by the claims appended hereto.

The invention we claim is:

1. A surgical method for reusing a surgical cable clamp with an orthopedic surgical cable for installation with respect to a patient's body, comprising:

providing an orthopedic surgical cable and a surgical cable clamp, the surgical cable clamp comprising a clamping body, a clamping mechanism, and a force application member;

orienting the surgical cable clamp relative to a bone in a patient's body;

securing a first portion of the orthopedic surgical cable relative to the clamping body;

capturing a second portion of the orthopedic surgical cable between the clamping mechanism and the clamping body, wherein the orthopedic surgical cable is wrapped around a portion of the patient's body;

connecting the force application member to the clamping body and the clamping mechanism;

gripping the second portion of the orthopedic surgical cable between the clamping body and clamping mechanism by rotating the force application member in a first direction so that the gripping is subject to gradual control by rotation of the force application member, thus creating a first tension in the orthopedic surgical cable;

releasing the first tension in the orthopedic surgical cable by rotating the force application member in an opposing direction to the first direction so that the orthopedic surgical cable can be repositioned between the clamping mechanism and the clamping body; and gripping the second portion of the orthopedic surgical cable between the clamping body and clamping mechanism by rotating the force application member in the first direction so that consequent gripping is subject to gradual control by rotation of the force application member, thus creating a second tension in the orthopedic surgical cable.

2. The method of claim 1, wherein:

securing a first portion of the orthopedic surgical cable relative to the clamping body further comprises:

restraining a larger end of the cable with the clamping body.

3. The method of claim 2, wherein the larger end of the cable is a fitting mounted to an end of the cable.

4. The method of claim 1, wherein the surgical cable clamp is incorporated into a prefabricated device selected from a group consisting of; an orthopedic device, a bone plate, or a troohanteric grip.

5. The method of claim 1, wherein the surgical cable clamp is a stand alone type device.

6. The method of claim 1, wherein:

gripping the second portion of the orthopedic surgical cable between the clamping body and clamping mechanism by rotating the force application member in a first direction so that the gripping is subject to gradual control by rotation of the force application member, further comprises:

forcing the clamping body and clamping mechanism apart from each other.

7. The method of claim 1, wherein:

gripping the second portion of the orthopedic surgical cable between the clamping body and clamping mechanism by rotating the force application member in a first direction so that the gripping is subject to gradual control by rotation of the force application member, further comprises:

forcing the clamping body and clamping mechanism towards each other.

8. The method of claim 1, wherein the force application member is a threaded force application member.

9. A surgical method for reusing a surgical cable clamp with an orthopedic surgical cable for installation with respect to a patient's body, comprising:

providing an orthopedic surgical cable and a surgical cable clamp, the surgical cable clamp comprising a clamping body, a clamping mechanism, and a force application member;

orienting the clamping body relative to a bone in a patient's body;

connecting a first portion of the orthopedic surgical cable to the clamping body;

wrapping a remaining portion of the orthopedic surgical cable around a part of a patient's bone;

connecting a second portion of the orthopedic surgical cable to the clamping body;

capturing the first portion and second portion of the orthopedic surgical cable between the clamping body and clamping mechanism, connecting the force application member to the clamping body and clamping mechanism;

gripping the first and second portions of the orthopedic surgical cable between the clamping body and the clamping mechanism by rotating the force application member in a first direction so that the consequent gripping is subject to gradual control by the force application member, thus creating a first tension in the otthopedic surgical cable;

releasing the first tension in the orthopedic surgical cable by rotating the force application member in a second direction so that the orthopedic surgical cable can be repositioned between the clamping mechanism and the clamping body; and gripping the first and second portions of the orthopedic surgical cable between the clamping body and the clamping mechanism by rotating the force application member in the first direction so that the consequent gripping is subject to gradual control by the force application member, thus creating a second tension in the orthopedic surgical cable.

10. The method of claim 9, wherein connecting a first portion of the orthopedic surgical cable to the clamping body further comprises:
restraining a larger end of the cable with the clamping body.

11. The method of claim 10, wherein the larger end of the cable is a fitting mounted to an end of the cable.

12. The method of claim 10, wherein the surgical cable clamp is incorporated into a prefabricated device selected from a group consisting of: an orthopedic device, a bone plate, or a trochanteric grip.

13. The method of claim 10, wherein the surgical cable clamp is a stand alone type device.

14. The method of claim 10, wherein:
gripping the first and second portions of the orthopedic surgical cable between the clamping body and the clamping mechanism by rotating the force application member in a first direction so that the consequent gripping is subject to gradual conhrol by the force application member, further comprises:
forcing the clamping body and clamping mechanism apart from each other.

15. The method of claim 9, wherein:
gripping the first and second portions of the orthopedic surgical cable between the clamping body and the clamping mechanism by rotating the force application member in a first direction so that the consequent gripping is subject to gradual control by the force application member, further comprises:
forcing the clamping body and clamping mechanism towards each other.

16. The method of claim 9, wherein the force application member is a threaded force application member.

17. A surgical method for reusing a surgical cable clamp with an orthopedic surgical cable for installation with respect to a patient's body, comprising:

providing an orthopedic surgical cable and a surgical cable clamp, the surgical cable clamp comprising a clamping body, a clamping mechanism, and a force application member;

orienting the surgical cable clamp relative to a bone in the patient's body;

securing a first portion of the orthopedic surgical cable with the surgical cable clamp;

wrapping a remaining portion of the orthopedic surgical cable around a part of the patient's bone;

capturing an extended portion of the orthopedic surgical cable between the clamping body and the clamping mechanism;

gripping the extended portion of the orthopedic surgical cable between the clamping body and the clamping mechanism by activating the force application member so that the consequent gripping is subject to gradual control by the force application member, thus creating a first tension in the orthopedic surgical cable;

deactivating the force application member so that the first tension can be released and the orthopedic surgical cable can be repositioned between the clamping mechanism and the clamping body; and gripping the extended portion of the orthopedic surgical cable between the clamping body and the clamping mechanism together by activating the force application member so that the clamping body and clamping mechanism grip the extended portion of the orthopedic surgical cable in a manner whereby the force and consequent gripping are subject to gradual control by the force application member, thus creating a second tension in the orthopedic surgical cable.

18. The method of claim 17, wherein the force application member is adapted to force the clamping body and clamping mechanism towards each other.

19. The method of claim 17, wherein the force application member is adapted to force the clamping body and clamping mechanism apart horn each other.

20. The method of claim 17, wherein:
the force application member is selected from a group consisting of:
an elastic member, a shape-memory member, a memory metal member, a heat activated member, a farce activated member, an electrically-activated member, and a magnetically-activated member.

21. The method of claim 17, wherein the fbrce application member is a threaded force application member.

22. A surgical method for reusing a surgical cable clamp with an orthopedic surgical cable for installation of a device with respect to a patient's body, comprising:
providing a device, an orthopedic surgical cable, and a surgical cable clamp, wherein the surgical cable clamp includes a force application member;

securing a first portion of the orthopedic surgical cable to the device;

orienting the device relative to a part of the patient's body;

wrapping an extended portion of the orthopedic surgical cable around a part of a patient's body;

capturing the extended portion of the orthopedic surgical cable between the surgical cable clamp and device;

connecting the force application member to the surgical cable clamp;

gripping the extended portion of the orthopedic surgical cable between the surgical cable clamp and device by rotating the force application member in a first direction so that the surgical cable clamp and device grip the extended portion of the orthopedic surgical cable in a manner whereby the consequent gripping is subject to gradual control by the force application member, thus creating a first tension in the orthopedic surgical cable;

releasing the first tension in the orthopedic surgical cable by rotating the force application member in a second direction so that the first tension can be released and the orthopedic surgical cable can be repositioned between the surgical cable clamp and device; and gripping the extended portion of the orthopedic surgical cable between the surgical cable clamp and device together by rotating the force application member in the first direction so that the surgical cable clamp and device grip the orthopedic surgical cable in a manner whereby consequent gripping is subject to gradual control by the force application member, thus creating a second tension in the orthopedic surgical cable.

23. The method of claim 22, wherein the device is selected from a group consisting of: an orthopedic device, a bone plate, and a trochanreric grip.

24. The method of claim 22, wherein the surgical cable clamp is incorporated into a prefabricated orthopedic device.

25. The method of claim 22, wherein the surgical cable clamp is a stand alone type device.

26. The method of claim 22, wherein the force application member is a threaded force application member.

* * * * *